US006063576A

United States Patent [19]
Keating et al.

[11] Patent Number: 6,063,576
[45] Date of Patent: May 16, 2000

[54] ACTIN MUTATIONS IN DILATED CARDIOMYOPATHY, A HERITABLE FORM OF HEART FAILURE

[75] Inventors: Mark T. Keating; Thomas M. Olson, both of Salt Lake City, Utah

[73] Assignee: University of Utah Research Foundation, Salt Lake City, Utah

[21] Appl. No.: 09/106,217

[22] Filed: Jun. 29, 1998

[51] Int. Cl.[7] .................................................. C12Q 1/68
[52] U.S. Cl. ........................ 435/6; 435/4; 435/5; 435/6; 435/7.1; 435/91.2; 536/22.1; 536/23.1; 536/24.3; 536/24.33; 436/518; 530/350; 530/387.1; 530/388.1
[58] Field of Search .............................. 800/8; 433/4, 5, 433/6, 7.1, 91.2; 536/22.1, 23.1, 24.3, 24.33; 436/518; 530/330, 387.1, 388.1

[56] References Cited

U.S. PATENT DOCUMENTS 5,840,477  11/1998  Seidman et al. ............................. 435/4

OTHER PUBLICATIONS

Bowles, Karla R., et al., "Gene Mapping of Familial Autosomal Dominant Dilated Cardiomyopathy to Chromosome 10q21–23", *J. Clin. Invest.,* vol. 98, No. 6, pp. 1355–1360, Sep. 1996.

Dec, M.D., G. William, and Fuster, M.D., PhD., Valentin, "Idiopathic Dilated Cardiomyopathy", *The New England Journal of Medicine,* vol. 331, No. 23, pp. 1564–1575, Dec., 1994.

Gimona, Mario, et al., "β–Actin Specific Monoclonal Antibody", *Cell Motility and the Cytoskeleton,* 27:108–116 (1994).

Gunning, Peter, et al, "α–Skeletal and α–Cardiac Actin Genes Are Coexpressed in Adult Human Skeletal Muscle and Heart", *Molecular and Cellular Biology,* vol. 3, No. 11, pp. 1985–1995, Nov., 1983.

Hamada, Hiroshi, et al., "Molecular structure and evolutionary orgin of human cardiac muscle actin gene". *Proc. Natl. Acad. Sci. USA,* vol. 79, pp. 5901–5905, Oct. 1982.

Hamada, Hiroshi and Kakunaga, Takeo, "Potential Z–DNA forming sequences are highly dispersed in the human genome", *Nature,* vol. 298, pp. 396–398, Jul., 1982.

Hennessey, Emma S., et al, "Molecular genetics of actin function", *Biochem J.,* (1993) 282, 657–671.

Herman, Ira M., "Actin isoforms", *Current Opinion in Cell Biology,* 1993, 5:48–55.

Kaspar, M.D., FACC, Edward K., et al., "The Causes of Dilated Cardiomyopathy: A Clinicopathologic Review of 673 Consecutive Patients", *JACC,* vol. 23, No. 3, pp. 586–590, Mar. 1994.

Kuhlman, Philip, et al., "The identification and characterisation of an actin–binding site in α–actinin by mutagenesis", *FEBS,* vol. 304, No. 2.3, pp. 201–206, Jun. 1992.

Kumar, A., et al. "Rescue of cardiac α–actin–deficient mice by enteric smooth muscle γ–actin", *Proc. Natl. Acad. Sci. USA,* vol. 94, pp. 4406–4411, Apr., 1997.

Levine, B.A., et al., "Binding sites involved in the interaction of actin with the N–terminal region of dystrophin", *FEBS,* vol. 298, No. 1, pp. 44–48, Feb., 1992.

Lu, Mei–Hua, et al., "The Vinculin/Sarcomeric–α–Actinin/α–Actin Nexus in Cultured Cardiac Myocytes", *The Journal of Cell Biology,* vol. 117, No. 5, pp. 1007–1022, Jun., 1992.

Manolio, MD, MHS, Teri A., et al., "Prevalence and Etiology of Idiopathic Dilated Cardiomyopathy (Summary of a National Heart, Lung, and Blood Institute Workshop)", *The American Journal of Cardiology,* vol. 69, pp. 1458–1466, Jun., 1992.

Mestroni, Luisa, et al., "Familial dilated cardiomyopathy", *Br. Heart J.,* 1994: 72 (Supplement):S 35–S 41.

Michels, MD, Virginia V., et al, "Familial Aggregation of Idiopathic Dilated Cardiomyopathy", *The American Journal of Cardiology,* vol. 55, pp. 1232–1233, Apr., 1995.

Michels, MD, Virginia V., et al., "The Frequency of Familial Dilated Cardiomyopathy in a Series of Patients with Idiopathic Dilated Cardiomyopathy", *The New England Journal of Medicine,* vol. 326, No. 2, pp. 77–82, Jan., 1992.

Minty, Adrian and Kedes, Larry, "Upstream Regions of the Human Cardiac Actin Gene That Modulate Its Transcription in Muscle Cells: Presence of an Evolutionarily Conserved Repeated Motif", *Molecular and Cellular Biology,* vol. 6, No. 6, pp. 2125–2136, Jun., 1986.

Olson, Timothy M., et al., "Actin Mutations in Dilated Cardiomyopathy, a Hertiable Form of Heart Failure", *Science,* vol. 280, pp. 750–752, May, 1998.

Olson, Timothy, M. and Keating, Mark T., "Mapping a Cardiomyopathy Locus to Chromosome 3p22–p25", *J. Clin. Invest,* vol. 97., No. 2, pp. 528–532, Jan., 1996.

Reisler, Emil, "Actin molecular structure and function", *Current Opinion in Cell Biology,* 1993, 5:41–47.

Vandekerckhove, Joël, et al., "Simultaneous Expression of Skeletal Muscle and Heart Actin Proteins in Various Striated Muscle Tissues and Cells", *The Journal of Biological Chemistry,* vol. 261, No. 4, pp. 1838–1843, Feb., 1986.

*Primary Examiner*—Kenneth R. Horlick
*Assistant Examiner*—Janell E. Taylor
*Attorney, Agent, or Firm*—Rothwell, Figg, Ernst & Kurz, P.C.

[57] ABSTRACT

Two mutations in the human cardiac actin gene are disclosed which have been associated with idiopathic dilated cardiomyopathy (IDC) in two families. These mutations cosegregate with IDC in the two families. Both mutations affect universally conserved amino acids in domains of actin that attach to Z bands and intercalated discs. Analysis of the cardiac actin gene can be used to determine the presence in a patient of IDC resulting from mutations in this gene. Such analysis is useful in the diagnosis and prognosis of the disease in patients with mutations in this gene.

33 Claims, 2 Drawing Sheets

6,063,576

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1134 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (ix) FEATURE:
      (A) NAME/KEY: CDS
      (B) LOCATION: 1..1131

(xi) SEQUENCE DESCRIPTION: SEQ ID NO:1:

```
ATG TGT GAC GAC GAG GAG ACC ACC GCC CTG GTG TGC GAC AAC GGC TCT         48
Met Cys Asp Asp Glu Glu Thr Thr Ala Leu Val Cys Asp Asn Gly Ser
 1               5                  10                  15

GGG CTG GTG AAG GCC GGC TTT GCG GGC GAT GAC GCG CCC CGC GCT GTC         96
Gly Leu Val Lys Ala Gly Phe Ala Gly Asp Asp Ala Pro Arg Ala Val
                 20                  25                  30

TTC CCG TCC ATC GTG GGC CGC CCG CGG CAC CAG GGA GTT ATG GTG GGT        144
Phe Pro Ser Ile Val Gly Arg Pro Arg His Gln Gly Val Met Val Gly
             35                  40                  45

ATG GGT CAG AAG GAC TCC TAC GTA GGT GAT GAA GCC CAG AGC AAG AGA        192
Met Gly Gln Lys Asp Ser Tyr Val Gly Asp Glu Ala Gln Ser Lys Arg
 50                  55                  60

GGC ATC CTG ACC CTG AAG TAT CCC ATC GAG CAT GGT ATC ATC ACC AAC        240
Gly Ile Leu Thr Leu Lys Tyr Pro Ile Glu His Gly Ile Ile Thr Asn
             65                  70                  75              80

TGG GAC GAC ATG GAG AAG ATC TGG CAC CAC ACC TTC TAC AAT GAG CTC        288
Trp Asp Asp Met Glu Lys Ile Trp His His Thr Phe Tyr Asn Glu Leu
                 85                  90                  95

CGT GTT GCT CCC GAG GAG CAC CCC ACC CTG CTC ACA GAG GCC CCG CTG        336
Arg Val Ala Pro Glu Glu His Pro Thr Leu Leu Thr Glu Ala Pro Leu
                100                 105                 110

AAC CCC AAG GCC AAC CGG GAG AAG ATG ACT CAG ATC ATG TTT GAG ACC        384
Asn Pro Lys Ala Asn Arg Glu Lys Met Thr Gln Ile Met Phe Glu Thr
            115                 120                 125

TTC AAT GTC CCT GCC ATG TAC GTG GCC ATC CAG GCA GTG CTA TCC CTG        432
Phe Asn Val Pro Ala Met Tyr Val Ala Ile Gln Ala Val Leu Ser Leu
130                 135                 140

TAT GCT TCT GGC CGT ACC ACA GGC ATT GTT CTG GAC TCT GGG GAT GGT        480
Tyr Ala Ser Gly Arg Thr Thr Gly Ile Val Leu Asp Ser Gly Asp Gly
145                 150                 155                 160

GTA ACT CAC AAT GTC CCC ATC TAT GAG GGC TAC GCT TTG CCC CAT GCC        528
Val Thr His Asn Val Pro Ile Tyr Glu Gly Tyr Ala Leu Pro His Ala
                165                 170                 175

ATC ATG CGT CTG GAT CTG GCT GGT CGG GAC CTC ACT GAC TAC CTC ATG        576
Ile Met Arg Leu Asp Leu Ala Gly Arg Asp Leu Thr Asp Tyr Leu Met
                180                 185                 190

AAG ATC CTC ACT GAG CGT GGC TAC TCC TTT GTC ACC ACT GCT GAA CGT        624
Lys Ile Leu Thr Glu Arg Gly Tyr Ser Phe Val Thr Thr Ala Glu Arg
            195                 200                 205

GAA ATT GTC CGT GAC ATT AAA GAG AAG CTG TGC TAT GTC GCC CTG GAT        672
Glu Ile Val Arg Asp Ile Lys Glu Lys Leu Cys Tyr Val Ala Leu Asp
            210                 215                 220

TTT GAG AAT GAG ATG GCC ACA GCT GCC TCT TCC TCC TCC TTG GAG AAG        720
Phe Glu Asn Glu Met Ala Thr Ala Ala Ser Ser Ser Ser Leu Glu Lys
225                 230                 235                 240

AGC TAT GAA CTG CCT GAT GGC CAA GTC ATC ACT ATC GGC AAT GAG CGC        768
Ser Tyr Glu Leu Pro Asp Gly Gln Val Ile Thr Ile Gly Asn Glu Arg
                245                 250                 255

TTC CGC TGT CCT GAG ACA CTC TTC CAG CCC TCC TTC ATT GGT ATG GAA        816
Phe Arg Cys Pro Glu Thr Leu Phe Gln Pro Ser Phe Ile Gly Met Glu
                260                 265                 270

TCT GCT GGC ATC CAT GAA ACA ACT TAC AAT AGC ATC ATG AAG TGT GAC        864
Ser Ala Gly Ile His Glu Thr Thr Tyr Asn Ser Ile Met Lys Cys Asp
            275                 280                 285

ATT GAT ATC CGC AAG GAC CTG TAT GCC AAC AAT GTC TTA TCT GGA GGC        912
Ile Asp Ile Arg Lys Asp Leu Tyr Ala Asn Asn Val Leu Ser Gly Gly
            290                 295                 300

ACC ACT ATG TAC CCT GGT ATT GCT GAT CGT ATG CAG AAG GAA ATC ACT        960
Thr Thr Met Tyr Pro Gly Ile Ala Asp Arg Met Gln Lys Glu Ile Thr
```

```
Thr Thr Met Tyr Pro Gly Ile Ala Asp Arg Met Gln Lys Glu Ile Thr
305                 310                 315                 320

GCT CTG GCT CCT AGC ACC ATG AAG ATT AAG ATT ATT GCT CCC CCT GAG      1008
Ala Leu Ala Pro Ser Thr Met Lys Ile Lys Ile Ile Ala Pro Pro Glu
                325                 330                 335

CGT AAA TAC TCT GTC TGG ATT GGG GGC TCC ATC TTG GCC TCT CTG TCC      1056
Arg Lys Tyr Ser Val Trp Ile Gly Gly Ser Ile Leu Ala Ser Leu Ser
            340                 345                 350

ACC TTC CAG CAA ATG TGG ATT AGC AAG CAA GAG TAC GAT GAG GCA GGC      1104
Thr Phe Gln Gln Met Trp Ile Ser Lys Gln Glu Tyr Asp Glu Ala Gly
        355                 360                 365

CCA TCC ATT GTC CAC CGC AAA TGC TTC TAA                              1134
Pro Ser Ile Val His Arg Lys Cys Phe
    370                 375
```

(2) INFORMATION FOR SEQ ID NO:2:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO:2:

```
Met Cys Asp Asp Glu Glu Thr Thr Ala Leu Val Cys Asp Asn Gly Ser
1               5                   10                  15

Gly Leu Val Lys Ala Gly Phe Ala Gly Asp Asp Ala Pro Arg Ala Val
            20                  25                  30

Phe Pro Ser Ile Val Gly Arg Pro Arg His Gln Gly Val Met Val Gly
        35                  40                  45

Met Gly Gln Lys Asp Ser Tyr Val Gly Asp Glu Ala Gln Ser Lys Arg
    50                  55                  60

Gly Ile Leu Thr Leu Lys Tyr Pro Ile Glu His Gly Ile Ile Thr Asn
65                  70                  75                  80

Trp Asp Asp Met Glu Lys Ile Trp His His Thr Phe Tyr Asn Glu Leu
                85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
    210                 215                 220

Phe Glu Asn Glu Met Ala Thr Ala Ala Ser Ser Ser Leu Glu Lys
225                 230                 235                 240

Ser Tyr Glu Leu Pro Asp Gly Gln Val Ile Thr Ile Gly Asn Glu Arg
                245                 250                 255
```

```
Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
            275                 280                 285

Ile Asp Ile Arg Lys Asp Leu Tyr Ala Asn Asn Val Leu Ser Gly Gly
290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ala Pro Pro Glu
                325                 330                 335

Arg Lys Tyr Ser Val Trp Ile Gly Gly Ser Ile Leu Ala Ser Leu Ser
            340                 345                 350

Thr Phe Gln Gln Met Trp Ile Ser Lys Gln Glu Tyr Asp Glu Ala Gly
            355                 360                 365

Pro Ser Ile Val His Arg Lys Cys Phe
            370                 375
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:3:

CCCCTGAAGC TGTGCCAAGA     20

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:4:

GGCTCGGCGG GAAGTTTAC     19

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:5:

TAAATGGACA AGACACTGAT TAT                                                    23

(2) INFORMATION FOR SEQ ID NO:6:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Primer"

(iii) HYPOTHETICAL: NO (iv) ANTI-SENSE: YES (xi) SEQUENCE DESCRIPTION: SEQ ID NO:6:

CAGCAAGGTC GGTGACTT                                                          18

(2) INFORMATION FOR SEQ ID NO:7:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Primer"

(iii) HYPOTHETICAL: NO (iv) ANTI-SENSE: NO (xi) SEQUENCE DESCRIPTION: SEQ ID NO:7:

GCTAGAGCAG TGGTGTTGTC                                                        20

(2) INFORMATION FOR SEQ ID NO:8:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Primer"

(iii) HYPOTHETICAL: NO (iv) ANTI-SENSE: YES (xi) SEQUENCE DESCRIPTION: SEQ ID NO:8:

AGGTAGGCGG ATTCAGTG                                                          18

(2) INFORMATION FOR SEQ ID NO:9:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Primer"

(iii) HYPOTHETICAL: NO (iv) ANTI-SENSE: NO (xi) SEQUENCE DESCRIPTION: SEQ ID NO:9:

CTCACTGAAT CCGCCTACCT                                               20

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:10:

CTACACCAGA CCCTACAACT C                                             21

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:11:

GACTCGTTCC CAGGTATG                                                 18

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:12:

GATCTCCCAC TCACAAAAG                                                19

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: NO (xi) SEQUENCE DESCRIPTION: SEQ ID NO:13:

```
AAGTTTTTGT TTTCTTCTGC                                         20
```

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (iv) ANTI-SENSE: YES (xi) SEQUENCE DESCRIPTION: SEQ ID NO:14:

```
CATAATACCG TCATCCTGA                                          19
```

(2) INFORMATION FOR SEQ ID NO:15:

(i) SEQUENCE CHARACTERISTICS:
        (A) LENGTH: 1128 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 1..1125

(xi) SEQUENCE DESCRIPTION: SEQ ID NO:15:

```
GAC GAC GAG GAG ACC ACC GCC CTG GTG TGC GAC AAC GGC TCT GGG CTG     48
Asp Asp Glu Glu Thr Thr Ala Leu Val Cys Asp Asn Gly Ser Gly Leu
 1               5                  10                  15

GTG AAG GCC GGC TTT GCG GGC GAT GAC GCG CCC CGC GCT GTC TTC CCG     96
Val Lys Ala Gly Phe Ala Gly Asp Asp Ala Pro Arg Ala Val Phe Pro
                20                  25                  30

TCC ATC GTG GGC CGC CCG CGG CAC CAG GGA GTT ATG GTG GGT ATG GGT    144
Ser Ile Val Gly Arg Pro Arg His Gln Gly Val Met Val Gly Met Gly
            35                  40                  45

CAG AAG GAC TCC TAC GTA GGT GAT GAA GCC CAG AGC AAG AGA GGC ATC    192
Gln Lys Asp Ser Tyr Val Gly Asp Glu Ala Gln Ser Lys Arg Gly Ile
        50                  55                  60

CTG ACC CTG AAG TAT CCC ATC GAG CAT GGT ATC ATC ACC AAC TGG GAC    240
Leu Thr Leu Lys Tyr Pro Ile Glu His Gly Ile Ile Thr Asn Trp Asp
 65                  70                  75                  80

GAC ATG GAG AAG ATC TGG CAC CAC ACC TTC TAC AAT GAG CTC CGT GTT    288
Asp Met Glu Lys Ile Trp His His Thr Phe Tyr Asn Glu Leu Arg Val
                 85                  90                  95

GCT CCC GAG GAG CAC CCC ACC CTG CTC ACA GAG GCC CCG CTG AAC CCC    336
Ala Pro Glu Glu His Pro Thr Leu Leu Thr Glu Ala Pro Leu Asn Pro
                100                 105                 110
```

```
AAG GCC AAC CGG GAG AAG ATG ACT CAG ATC ATG TTT GAG ACC TTC AAT      384
Lys Ala Asn Arg Glu Lys Met Thr Gln Ile Met Phe Glu Thr Phe Asn
        115                 120                 125

GTC CCT GCC ATG TAC GTG GCC ATC CAG GCA GTG CTA TCC CTG TAT GCT      432
Val Pro Ala Met Tyr Val Ala Ile Gln Ala Val Leu Ser Leu Tyr Ala
    130                 135                 140

TCT GGC CGT ACC ACA GGC ATT GTT CTG GAC TCT GGG GAT GGT GTA ACT      480
Ser Gly Arg Thr Thr Gly Ile Val Leu Asp Ser Gly Asp Gly Val Thr
145                 150                 155                 160

CAC AAT GTC CCC ATC TAT GAG GGC TAC GCT TTG CCC CAT GCC ATC ATG      528
His Asn Val Pro Ile Tyr Glu Gly Tyr Ala Leu Pro His Ala Ile Met
                165                 170                 175

CGT CTG GAT CTG GCT GGT CGG GAC CTC ACT GAC TAC CTC ATG AAG ATC      576
Arg Leu Asp Leu Ala Gly Arg Asp Leu Thr Asp Tyr Leu Met Lys Ile
            180                 185                 190

CTC ACT GAG CGT GGC TAC TCC TTT GTC ACC ACT GCT GAA CGT GAA ATT      624
Leu Thr Glu Arg Gly Tyr Ser Phe Val Thr Thr Ala Glu Arg Glu Ile
        195                 200                 205

GTC CGT GAC ATT AAA GAG AAG CTG TGC TAT GTC GCC CTG GAT TTT GAG      672
Val Arg Asp Ile Lys Glu Lys Leu Cys Tyr Val Ala Leu Asp Phe Glu
    210                 215                 220

AAT GAG ATG GCC ACA GCT GCC TCT TCC TCC TCC TTG GAG AAG AGC TAT      720
Asn Glu Met Ala Thr Ala Ala Ser Ser Ser Ser Leu Glu Lys Ser Tyr
225                 230                 235                 240

GAA CTG CCT GAT GGC CAA GTC ATC ACT ATC GGC AAT GAG CGC TTC CGC      768
Glu Leu Pro Asp Gly Gln Val Ile Thr Ile Gly Asn Glu Arg Phe Arg
                245                 250                 255

TGT CCT GAG ACA CTC TTC CAG CCC TCC TTC ATT GGT ATG GAA TCT GCT      816
Cys Pro Glu Thr Leu Phe Gln Pro Ser Phe Ile Gly Met Glu Ser Ala
            260                 265                 270

GGC ATC CAT GAA ACA ACT TAC AAT AGC ATC ATG AAG TGT GAC ATT GAT      864
Gly Ile His Glu Thr Thr Tyr Asn Ser Ile Met Lys Cys Asp Ile Asp
        275                 280                 285

ATC CGC AAG GAC CTG TAT GCC AAC AAT GTC TTA TCT GGA GGC ACC ACT      912
Ile Arg Lys Asp Leu Tyr Ala Asn Asn Val Leu Ser Gly Gly Thr Thr
    290                 295                 300

ATG TAC CCT GGT ATT GCT GAT CGT ATG CAG AAG GAA ATC ACT GCT CTG      960
Met Tyr Pro Gly Ile Ala Asp Arg Met Gln Lys Glu Ile Thr Ala Leu
305                 310                 315                 320

GCT CCT AGC ACC ATG AAG ATT AAG ATT ATT GCT CCC CCT GAG CGT AAA     1008
Ala Pro Ser Thr Met Lys Ile Lys Ile Ile Ala Pro Pro Glu Arg Lys
                325                 330                 335

TAC TCT GTC TGG ATT GGG GGC TCC ATC TTG GCC TCT CTG TCC ACC TTC     1056
Tyr Ser Val Trp Ile Gly Gly Ser Ile Leu Ala Ser Leu Ser Thr Phe
            340                 345                 350

CAG CAA ATG TGG ATT AGC AAG CAA GAG TAC GAT GAG GCA GGC CCA TCC     1104
Gln Gln Met Trp Ile Ser Lys Gln Glu Tyr Asp Glu Ala Gly Pro Ser
        355                 360                 365

ATT GTC CAC CGC AAA TGC TTC TAA                                     1128
Ile Val His Arg Lys Cys Phe
    370                 375

(2) INFORMATION FOR SEQ ID NO:16:

(i) SEQUENCE CHARACTERISTICS:
        (A) LENGTH: 375 amino acids
        (B) TYPE: amino acid
        (D) TOPOLOGY: linear (ii) MOLECULE TYPE: protein (xi) SEQUENCE DESCRIPTION: SEQ ID NO:16:
```

```
Asp Asp Glu Glu Thr Thr Ala Leu Val Cys Asp Asn Gly Ser Gly Leu
 1               5                  10                 15

Val Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
        50                  55                  60

Leu Thr Leu Lys Tyr Pro Ile Glu His Gly Ile Ile Thr Asn Trp Asp
 65                 70                  75                  80

Asp Met Glu Lys Ile Trp His His Thr Phe Tyr Asn Glu Leu Arg Val
                85                  90                  95

Ala Pro Glu Glu His Pro Thr Leu Leu Thr Glu Ala Pro Leu Asn Pro
            100                 105                 110

Lys Ala Asn Arg Glu Lys Met Thr Gln Ile Met Phe Glu Thr Phe Asn
            115                 120                 125

Val Pro Ala Met Tyr Val Ala Ile Gln Ala Val Leu Ser Leu Tyr Ala
            130                 135                 140

Ser Gly Arg Thr Thr Gly Ile Val Leu Asp Ser Gly Asp Gly Val Thr
145                 150                 155                 160

His Asn Val Pro Ile Tyr Glu Gly Tyr Ala Leu Pro His Ala Ile Met
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Val Thr Thr Ala Glu Arg Glu Ile
            195                 200                 205

Val Arg Asp Ile Lys Glu Lys Leu Cys Tyr Val Ala Leu Asp Phe Glu
210                 215                 220

Asn Glu Met Ala Thr Ala Ala Ser Ser Ser Ser Leu Glu Lys Ser Tyr
225                 230                 235                 240

Glu Leu Pro Asp Gly Gln Val Ile Thr Ile Gly Asn Glu Arg Phe Arg
            245                 250                 255

Cys Pro Glu Thr Leu Phe Gln Pro Ser Phe Ile Gly Met Glu Ser Ala
            260                 265                 270

Gly Ile His Glu Thr Thr Tyr Asn Ser Ile Met Lys Cys Asp Ile Asp
            275                 280                 285

Ile Arg Lys Asp Leu Tyr Ala Asn Asn Val Leu Ser Gly Gly Thr Thr
            290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ala Gly Pro Ser
            355                 360                 365

Ile Val His Arg Lys Cys Phe
            370                 375

(2) INFORMATION FOR SEQ ID NO:17:

(i) SEQUENCE CHARACTERISTICS:
          (A) LENGTH: 63 base pairs
          (B) TYPE: nucleic acid
```

-continued

```
        (C) STRANDEDNESS: single
        (D) TOPOLOGY: linear (ii) MOLECULE TYPE: other nucleic acid
        (A) DESCRIPTION: /desc = "Hypothetical fragment"

(iii) HYPOTHETICAL: YES (xi) SEQUENCE DESCRIPTION: SEQ ID NO:17:

ACCGTAGCTA CGTACGTATA TAGAAAGGGC GCGATCGTCG TCGCGTATGA CGACTTAGCA      60

TGC                                                                   63

(2) INFORMATION FOR SEQ ID NO:18:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Hypothetical nucleic acid"

(iii) HYPOTHETICAL: YES (xi) SEQUENCE DESCRIPTION: SEQ ID NO:18:

ACCGGTAGCT ACGTACGTTA TTTAGAAAGG GGTGTGTGTG TGTGTGTAAA CCGGGGTTTT      60

CGGGATCGTC CGTCGCGTAT GACGACTTAG CCATGCACGG TATATCGTAT TAGGACTAGC    120

GATTGACTAG                                                           130
```

ACTIN MUTATIONS IN DILATED CARDIOMYOPATHY, A HERITABLE FORM OF HEART FAILURE

This application was made with Government support under an NIH SCOR grant (Grant No. 5-P50-HL-53773) funded by the National Institutes of Health, Bethesda, Md. and Public Health Services Research Grant M01-RR00064 from the National Center for Research Resources. The U.S. Government has certain rights in this invention.

BACKGROUND OF THE INVENTION

Heart failure is a major medical problem that affects 700 thousand individuals per year in the United States and accounts for annual costs of 10 to 40 billion dollars (Abraham and Bristow, 1997). Heart failure is the primary manifestation of dilated cardiomyopathy, a group of disorders characterized by cardiac dilation and pump dysfunction. Half of patients with dilated cardiomyopathy are diagnosed with idiopathic dilated cardiomyopathy (IDC), isolated heart failure of unknown etiology (affecting 5 to 8 in 100,000 individuals) (Manolio et al., 1992; Kasper et al., 1994). Cardiac transplantation is the only definitive treatment for end-stage disease.

IDC is hereditary in at least 20% of cases (Michels et al., 1992), indicating that genetic factors are important in its pathogenesis. In both familial and non-familial IDC, disease onset is delayed (mean age at diagnosis=45±17 years) and the five-year mortality rate is 50% after symptoms develop (Michels et al., 1992; Dec and Fuster, 1994). Consequently, few multigeneration IDC families with many affected, living individuals have been identified. Although chromosomal loci for IDC (1p1-q1, 1q32, 3p22–25, 9q13-q22, 10q21-q23) have been identified by genetic linkage analysis in rare families (Mendelian Inheritance in Man, Numbers 115200, 600884, 601154, 601493, and 601494; Olson and Keating, 1997; Bowles et al., 1996), these families are too small for positional cloning of IDC genes. Furthermore, these loci do not identify all potential candidate genes, like cardiac actin (ACTC) on chromosome 15q14. As an alternative strategy, the research disclosed herein used a candidate gene approach in small IDC families.

The present invention is directed to ACTC and its gene products, mutations in the gene, the mutated gene, probes for the wild-type and mutated gene, and to a process for the diagnosis and prevention of idiopathic dilated cardiomyopathy. The instant work shows that some families with idiopathic dilated cardiomyopathy have mutations in ACTC. Idiopathic dilated cardiomyopathy is diagnosed in accordance with the present invention by analyzing the DNA sequence of the ACTC gene of an individual to be tested and comparing the respective DNA sequence to the known DNA sequence of normal ACTC. Alternatively, the ACTC gene of an individual to be tested can be screened for mutations which cause idiopathic dilated cardiomyopathy.

The publications and other materials used herein to illuminate the background of the invention or provide additional details respecting the practice, are incorporated by reference, and for convenience are respectively grouped in the appended List of References.

SUMMARY OF THE INVENTION

The present invention demonstrates a molecular basis of hereditary idiopathic dilated cardiomyopathy. More specifically, the present invention has determined that molecular variants of the ACTC gene cause or are involved in the pathogenesis of idiopathic dilated cardiomyopathy. Genotypic analyses show that ACTC is linked to dilated cardiomyopathy in two unrelated families. Analysis of the ACTC gene will provide an early identification of subjects likely to develop or who already have idiopathic dilated cardiomyopathy. The diagnostic method comprises analyzing the DNA sequence of the ACTC gene of an individual to be tested and comparing it with the DNA sequence of the native, non-variant gene. In a second embodiment, the ACTC gene of an individual to be tested is screened for mutations which cause idiopathic dilated cardiomyopathy.

SUMMARY OF SEQUENCE LISTING

Figure 1A:
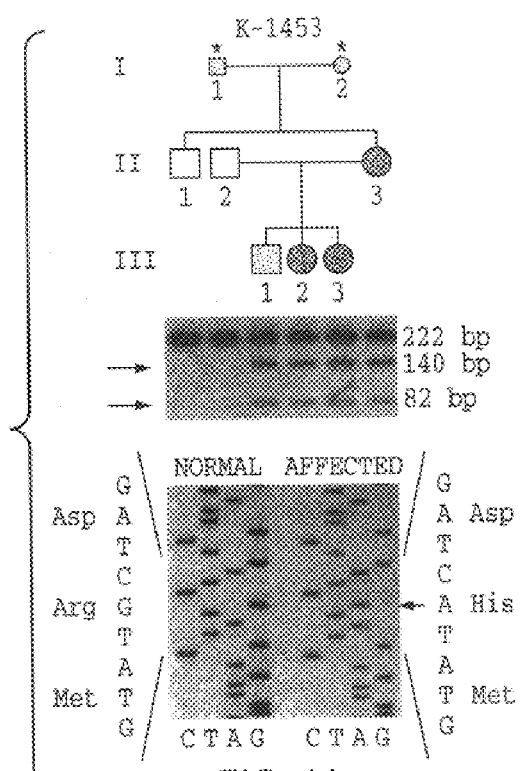
FIGS. 1A–1B. ACTC missense mutations in two IDC families. Pedigree symbols designate the following traits: circles=females, squares=males, diagonal lines=deceased, filled=IDC, half-filled=LV dilation or borderline LV size, empty=normal, shaded=uncertain, *=insufficient data because of death (I.1 and I.2, K-9695), pre-existing ischemic heart disease (I.1, K-1453), or refusal to participate (I.2, K-1453). Spouses were classified as normal. (A) Below K-1453, the results of PCR-RFLP and sequence analyses for exon 5 are shown. The 222 bp PCR product of primer pairs 5F/5R was digested with Bcl I. The mutation creates a unique Bcl I site, resulting in 140-bp and 82-bp fragments (arrows) that cosegregate with IDC. Sequence analysis reveals a G-to-A point mutation, resulting in a conservative histidine-to-arginine substitution. (B) Below K-9695, the results of SSCP and sequence analyses for exon 6 are shown. The anomalous conformer (arrow) cosegregates with IDC. Sequence analysis reveals an A-to-G point mutation, resulting in a nonconservative glycine-to-glutamic acid substitution.

SEQ ID NO: 1 is the full length cDNA for wild-type ACTC.

SEQ ID NO: 2 is the full length ACTC encoded by SEQ ID NO: 1.

SEQ ID NOs: 3–14 are primers for sequencing across the 6 exons of ACTC. These are used in pairs, with SEQ ID NOs: 3 and 4 used to sequence across exon 1, SEQ ID NOs: 5 and 6 used to sequence across exon 2, etc.

SEQ ID NO: 15 is a cDNA encoding wild-type ACTC without the initial two codons which encode Met-Cys which are posttranslationally removed.

SEQ ID NO: 16 is ACTC without the initial Met-Cys which is posttranslationally removed.

SEQ ID NOs: 17 and 18 are hypothetical nucleic acids used to demonstrate a method of calculating percent homology.

DETAILED DESCRIPTION OF THE INVENTION

The present invention is directed to the determination that idiopathic dilated cardiomyopathy (IDC) maps to the ACTC gene and that molecular variants of this gene cause or are involved in the pathogenesis of IDC. More specifically, the present invention relates to mutations in the ACTC gene and its use in the diagnosis of IDC. The present invention is further directed to methods of screening humans for the presence of ACTC gene variants which cause IDC. Since IDC can now be detected earlier (i.e., before symptoms appear) and more definitively, better treatment options will be available in those individuals identified as having IDC. Some of the treatments presently used for IDC include lasix or diuretics for heart failure, β-agonists, β-receptor agonists, and in extreme cases, heart transplant. The present invention is also directed to methods for screening for drugs useful in treating or preventing IDC.

Two families with IDC were studied and for each it was found that family members with IDC have a point mutation in the ACTC gene, one being in codon 312 (Arg312His) and the other in codon 361 (Glu361Gly). The mutations segregated with the disease and were not found in unrelated controls. ACTC is one of six actin genes in humans (Mendelian Inheritance in Man # 102540), none of which previously had been implicated in human disease. In cardiac myocytes, cardiac actin is the main component of the thin filament of the sarcomere. One end of the polarized actin filament forms cross-bridges with myosin and the other end is immobilized, attached to a Z band or an intercalated disc (Holmes et al., 1990; Gregorio, 1997; Lu et al., 1992). Thus, actin transmits force between adjacent sarcomeres and neighboring myocytes to effect coordinated contraction of the heart. The mutations we identified occur in subdomains 1 and 3 of the actin monomer that form the immobilized end of the actin filament. Moreover, the Glu361Gly substitution is within a common binding domain for actinin, a protein comprising Z bands and intercalated discs, and dystrophin, a protein linking myofibrils to the extracellular matrix (Levine et al., 1992; Kuhlman et al., 1992).

In addition to our data, several lines of evidence support the hypothesis that relatively subtle molecular defects in force-transmitting proteins, like actin, lead to myocyte dysfunction and heart failure. First, missense mutations throughout the actin gene in Drosophila result in abnormal structure and function of flight muscle (Hennessey et al., 1993). Second, transgenic expression of a noncardiac actin in cardiac actin-deficient mice causes cardiac enlargement and dysfunction, resembling human DCM (Kumar et al., 1997). Third, missense mutations in dystrophin have been identified in X-linked dilated cardiomyopathy (Mendelian Inheritance in Man #302045; Ortiz-Lopez et al., 1997). In mice, heterozygous disruption of ACTC is not associated with heart abnormalities (Kumar et al., 1997). Thus, the missense mutations in ACTC defined here likely lead to altered actin function rather than loss of function.

Hypertrophic cardiomyopathy (HCM) is characterized by hypertrophy of the heart, in contrast to IDC which leads to chamber dilation and heart failure. The genes implicated in HCM all encode proteins involved in generation of force (beta-myosin heavy-chain, cardiac troponin T, alpha-tropomyosin, myosin-binding protein C, and essential and regulatory myosin light chains) (Spirito et al., 1997). This has led to the hypothesis that HCM is caused by chronic reduction of force generation, which stimulates secondary myocyte hypertrophy (Lankford et al., 1995; Watkins et al., 1996). The cellular mechanism underlying IDC, however, may not involve force generation. Actin provides a scaffold for force generation by interacting with myosin, but the mutations we identified are not in regions that interact with myosin (Reisler, 1993). Instead of generating force, actin transmits force to adjacent sarcomeres and myocytes, and, like dystrophin, transmits force to the extracellular matrix. Further evidence that IDC does not result from a primary defect in force generation is that pathologic features of HCM are not observed during the course of IDC. We proposed that IDC results from an episodic defect in force transmission. This defect may predispose affected myocytes to mechanical injury and cumulative cell death, secondary interstitial fibrosis, and cardiac dilation, a degenerative process that may take decades to develop.

The present invention provides methods of screening the ACTC gene to identify mutations. Such methods may further comprise the step of amplifying a portion of the ACTC gene, and may further include a step of providing a set of polynucleotides which are primers for amplification of said portion of the ACTC gene. The method is useful for identifying mutations for use in either diagnosis of IDC or prognosis of IDC.

Finally, the present invention is directed to a method for screening drug candidates to identify drugs useful for treating or preventing IDC. Drug screening is performed by comparing the binding of ACTC to its binding proteins (e.g., myosin, actinin and dystrophin) in the presence and absence of drug candidates. Drug screening can also be performed by administering drugs to persons or animals which have mutations in ACTC which cause IDC.

Proof that the ACTC gene is involved in causing IDC is obtained by finding sequences in DNA extracted from affected kindred members which create abnormal ACTC gene products or abnormal levels of the gene products. Such IDC susceptibility alleles will co-segregate with the disease in large kindreds. They will also be present at a much higher frequency in non-kindred individuals with IDC than in individuals in the general population. The key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

According to the diagnostic and prognostic method of the present invention, alteration of the wild-type ACTC gene is detected. In addition, the method can be performed by detecting the wild-type ACTC gene and confirming the lack of a cause of IDC as a result of this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germ-line mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the ACTC gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

The presence of IDC may be ascertained by testing any tissue of a human for mutations of the ACTC gene. For example, a person who has inherited a germline ACTC mutation would be prone to develop IDC. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the ACTC gene. Alteration of a wild-type ACTC allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of IDC cases. Southern blots displaying hybridizing fragments differing in length from control DNA when probed with sequences near or including the ACTC locus indicate a possible mutation. If restriction enzymes which produce very large restriction fragments are used, then pulsed field gel electrophoresis (PFGE) is employed.

Detection of point mutations may be accomplished by molecular cloning of the ACTC allele and sequencing the allele using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Ruano and Kidd, 1989). For allele-specific PCR, primers are used which hybridize at their 3' ends to a particular ACTC mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type ACTC gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the ACTC gene can also be detected using Southern hybridization, especially if the changes are gross rearrangements, such as deletions and insertions.

DNA sequences of the ACTC gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified ACTC sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Editorial, Nature Genetics, 1996). Also see Fodor (1997).

The most definitive test for mutations in a candidate locus is to directly compare genomic ACTC sequences from patients with those from a control population. Alternatively, one could sequence messenger RNA after amplification, e.g., by PCR, thereby eliminating the necessity of determining the exon structure of the candidate gene.

Mutations from patients falling outside the coding region of ACTC can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of ACTC mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type ACTC protein. For example, monoclonal antibodies immunoreactive with ACTC can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered ACTC protein can be used to detect alteration of the wild-type ACTC gene. Functional assays, such as protein binding determinations, can be used. In addition, assays can be used which detect ACTC biological function. Finding a mutant ACTC gene product indicates alteration of a wild-type ACTC gene.

A mutant ACTC gene or gene product can also be detected in other human body samples, such as serum, stool, urine and sputum. The same techniques discussed above for detection of mutant genes or gene products in tissues can be applied to other body samples. By screening such body samples, a simple early diagnosis (although it must be remembered that only a fraction of IDC cases result from ACTC mutations) or prognosis can be achieved for IDC resulting from a mutation in the ACTC gene.

The primer pairs of the present invention are useful for determination of the nucleotide sequence of a particular ACTC allele using PCR. The pairs of single-stranded DNA primers for ACTC can be annealed to sequences within or surrounding the ACTC gene on chromosome 15 in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular ACTC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from ACTC sequence or sequences adjacent to ACTC, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of ACTC, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the ACTC gene or mRNA using other techniques.

It has been discovered that most individuals with the wild-type ACTC gene do not have IDC. However, mutations which interfere with the function of the ACTC gene product are involved in the pathogenesis of IDC. Thus, the presence of an altered (or a mutant) ACTC gene which produces a protein having a loss of function, or altered function, directly causes IDC which increases the risk of heart failure. In order to detect an ACTC gene mutation, a biological sample is prepared and analyzed for a difference between the sequence of the allele being analyzed and the sequence of the wild-type allele. Mutant ACTC alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

Definitions

The present invention employs the following definitions.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis el al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the ACTC region are preferably complementary to, and hybridize specifically to sequences in the ACTC region or in regions that flank a target region therein. ACTC sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf etal., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the ACTC polypeptide and fragments thereof or to polynucleotide sequences from the ACTC region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the ACTC polypeptide or fragment. Monoclonal antibodies may be made by injecting mice with the protein polypeptides, fusion proteins or fragments thereof. Monoclonal antibodies will be screened by ELISA and tested for specific immunoreactivity with ACTC polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. In addition, as disclosed herein, ACTC binds to or interacts with myosin, actinin and dystrophin. Each of these proteins is also considered to be a binding partner of ACTC. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"ACTC Allele" refers to normal alleles of the ACTC locus as well as alleles of ACTC carrying variations that cause IDC.

"ACTC Locus", "ACTC Gene", "ACTC Nucleic Acids" or "ACTC Polynucleotide" each refer to polynucleotides, all of which are in the ACTC region, that are likely to be expressed in normal tissue, certain alleles of which result in IDC. The ACTC locus is intended to include coding sequences, intervening sequences and regulatory elements controlling transcription and/or translation. The ACTC locus is intended to include all allelic variations of the DNA sequence.

These terms, when applied to a nucleic acid, refer to a nucleic acid which encodes a human ACTC polypeptide, fragment, homolog or variant, including, e.g., protein fusions or deletions. The nucleic acids of the present invention will possess a sequence which is either derived from, or substantially similar to a natural ACTC-encoding gene or one having substantial homology with a natural ACTC-encoding gene or a portion thereof.

The ACTC gene or nucleic acid includes normal alleles of the ACTC gene, including silent alleles having no effect on the amino acid sequence of the ACTC polypeptide as well as alleles leading to amino acid sequence variants of the ACTC polypeptide that do not substantially affect its function. These terms also include alleles having one or more mutations which adversely affect the function of the ACTC polypeptide. A mutation may be a change in the ACTC nucleic acid sequence which produces a deleterious change in the amino acid sequence of the ACTC polypeptide, resulting in partial or complete loss of ACTC function, or may be a change in the nucleic acid sequence which results in the loss of effective ACTC expression or the production of aberrant forms of the ACTC polypeptide.

The ACTC nucleic acid may be that shown in SEQ ID NO: 1 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NO: 1 yet encode a polypeptide with the same amino acid sequence as shown in SEQ ID NO: 2. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO: 2. Nucleic acid encoding a polypeptide which is an amino acid sequence variant, derivative or allele of the amino acid sequence shown in SEQ ID NO: 2 is also provided by the present invention. Furthermore, the initial Met-Cys of the encoded polypeptide is post-translationally removed. Therefore nucleic acids similar to SEQ ID NO: 1 but without the initial 2 codons are also envisioned as well as any nucleic acid encoding a polypeptide of SEQ ID NO: 2 minus the initial Met-Cys. The shortened version of the gene and encoded polypeptide are shown as SEQ ID NOs: 15 and 16, respectively.

The ACTC gene also refers to (a) any DNA sequence that (i) hybridizes to the complement of the DNA sequences that encode the amino acid sequence set forth in SEQ ID NO: 2 or SEQ ID NO: 16 under highly stringent conditions (Ausubel et al., 1992) and (ii) encodes a gene product functionally equivalent to ACTC, or (b) any DNA sequence that (i) hybridizes to the complement of the DNA sequences that encode the amino acid sequence set forth in SEQ ID NO: 2 or SEQ ID NO: 16 under less stringent conditions, such as moderately stringent conditions (Ausubel et al., 1992) and (ii) encodes a gene product functionally equivalent to ACTC. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the ACTC region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an ACTC-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the ACTC locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides, or any number of nucleotides between 500 and the number shown in SEQ ID NO: 1 or SEQ ID NO: 15. The present invention includes all novel nucleic acids having at least 8 nucleotides derived from SEQ ID NO: 1 or SEQ ID NO: 15, its complement or functionally equivalent nucleic acid sequences. The present invention does not include nucleic acids which exist in the prior art. That is, the present invention includes all nucleic acids having at least 8 nucleotides derived from SEQ ID NO: 1 or SEQ ID NO: 15 with the proviso that it does not include nucleic acids existing in the prior art.

"ACTC protein" or "ACTC polypeptide" refers to a protein or polypeptide encoded by the ACTC locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native ACTC sequence, preferably in excess of about 90%, and more preferably at least about 95% homologous. Also included are proteins encoded by DNA which hybridize under high or low stringency conditions, to ACTC-encoding nucleic acids and closely related polypeptides or proteins retrieved by antisera to the ACTC protein (s).

The ACTC polypeptide may be that shown in SEQ ID NO: 2 or SEQ ID NO: 16 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the ACTC polypeptide. Such polypeptides may have an amino acid sequence which differs from that set forth in SEQ ID NO: 2 or SEQ ID NO: 16 by one or more of addition, substitution, deletion or insertion of one or more amino acids. Preferred such polypeptides have ACTC function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the ACTC polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of the ACTC polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural ACTC polypeptide.

"Probes". Polynucleotide polymorphisms associated with ACTC alleles which predispose to IDC are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of an ACTC susceptibility allele.

Probes for ACTC alleles may be derived from the sequences of the ACTC region, its cDNA, functionally equivalent sequences, or the complements thereof. The probes may be of any suitable length, which span all or a portion of the ACTC region, and which allow specific hybridization to the region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding ACTC are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides, or any number of nucleotides between 500 and the number of nucleotides in SEQ ID NO: 1 or SEQ ID NO: 15. The probes may also be used to determine whether mRNA encoding ACTC is present in a cell or tissue. The present invention includes all novel probes having at least 8 nucleotides derived from SEQ ID NO: 1 or SEQ ID NO: 15, its complement or functionally equivalent nucleic acid sequences. The present invention does not include probes which exist in the prior art. That is, the present invention includes all probes having at least 8 nucleotides derived from SEQ ID NO: 1 or SEQ ID NO: 15 with the proviso that they do not include probes existing in the prior art.

Similar considerations and nucleotide lengths are also applicable to primers which may be used for the amplification of all or part of the ACTC gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding ACTC is present in a cell or tissue. The present invention includes all novel primers having at least 8 nucleotides derived from the ACTC locus for amplifying the ACTC gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for ACTC polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$p, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of ACTC polypeptides. Immunological activities include both immunogenic function in a target immune system, as well as sharing of immunological epitopes for binding, serving as either a competitor or substitute antigen for an epitope of the ACTC protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for ACTC polypeptides or fragments thereof is described below.

The present invention also provides for fusion polypeptides, comprising ACTC polypeptides and fragments. Homologous polypeptides may be fusions between two or more ACTC polypeptide sequences or between the sequences of ACTC and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski etal., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the ACTC polypeptides from other biological material, such as from cells transformed with recombinant nucleic acids encoding ACTC, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

An ACTC protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

To determine homology between two different nucleic acids, the percent homology is to be determined using the BLASTN program "BLAST 2 sequences". This program is available for public use from the National Center for Biotechnology Information (NCBI) over the Internet (http://www.ncbi.nlm.nih.gov/gorf/b12.html) (Altschul et al., 1997). The parameters to be used are whatever combination of the following yields the highest calculated percent homology (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining homology herein, the percent homology refers to the shorter of the two sequences being compared. If any one region is shown in different alignments with differing percent identities, the alignments which yield the greatest homology are to be used. The averaging is to be performed as in this example of SEQ ID NOs: 17 and 18.

(SEQ ID NO:17)
5'-ACCGTAGCTACGTACGTATATAGAAAGGGCGCGATCGTCGTCGCGTAT

GACGACTTAGCATGC-3'

(SEQ ID NO:18)
5'-ACCGGTAGCTACGTACGTTATTTAGAAAGGGGTGTGTGTGTGTGTGTA

AACCGGGGTTTTCGGGATCGTCCGTCGCGTATGACGACTTAGCCATGCACG

GTATATCGTATTAGGACTAGCGATTGACTAG-3'

The program "BLAST 2 Sequences" shows differing alignments of these two nucleic acids depending upon the parameters which are selected. As examples, four sets of parameters were selected for comparing SEQ ID NOs: 17 and 18 (gap x_dropoff was 50 for all cases), with the results shown in fable 1. It is to be noted that none of the sets of parameters selected as shown in Table 1 is necessarily the best set of parameters for comparing these sequences. The percent homology is calculated by multiplying for each region showing identity the fraction of bases of the shorter strand within a region times the percent identity for that region and adding all of these together. For example, using the first set of parameters shown in Table 1, SEQ ID NO: 17 is the short sequence (63 bases), and two regions of identity are shown, the first encompassing bases 4–29 (26 bases) of SEQ ID NO: 17 with 92% identity to SEQ ID NO: 18 and the second encompassing bases 39–59 (21 bases) of SEQ ID NO: 17 with 100% identity to SEQ ID NO: 18.

Bases 1–3, 30–38 and 60–63 (16 bases) are not shown as having any identity with SEQ ID NO: 18. Percent homology is calculated as: (26/63)(92)+(21/63)(100)+(16/63)(0)= 71.3% homology. The percents of homology calculated using each of the four sets of parameters shown are listed in Table 1. Several other combinations of parameters are possible, but they are not listed for the sake of brevity. It is seen that each set of parameters resulted in a different calculated percent homology. Because the result yielding the highest percent homology is to be used, based solely on these four sets of parameters one would state that SEQ ID NOs: 17 and 18 have 87.1% homology. Again it is to be noted that use of other parameters may show an even higher homology for SEQ ID NOs: 17 and 18, but for brevity not all the possible results are shown.

TABLE 1

| | Parameter Values | | | | |
|---|---|---|---|---|---|
| Match | Mis-match | Open Gap | Extension Gap | Regions of identity (%) | Homology |
| 1 | −2 | 5 | 1 | 4–29 of 17 and 5–31 of 18 (92%) | 39–59 of 17 and 71–91 of 18 (100%) | 71.3 |
| 1 | −2 | 2 | 1 | 4–29 of 17 and 5–31 of 18 (92%) | 33–63 of 17 and 64–96 of 18 (93%) | 83.7 |
| 1 | −1 | 5 | 1 | — | 30–59 of 17 and 61–91 of 18 (93%) | 44.3 |
| 1 | −1 | 2 | 1 | 4–29 of 17 and 5–31 of 18 (92%) | 30–63 of 17 and 61–96 of 18 (91%) | 87.1 |

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type ACTC nucleic acid or wild-type ACTC polypeptide. The modified polypeptide will be substantially homologous to the wild-type ACTC polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type ACTC polypeptide. Alternatively, the similarity of function (activity) of the modified polypeptide may be higher than the activity of the wild-type ACTC polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type ACTC gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of recombinant or chemically synthesized nucleic acids vectors, transformation, host cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Caruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with the ACTC gene. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the ACTC nucleic acid or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of ACTC polypeptide.

The probes and primers based on the ACTC gene sequence disclosed herein are used to identify homologous ACTC gene sequences and proteins in other species. These gene sequences and proteins are used in the diagnostic/prognostic, therapeutic and drug screening methods described herein for the species from which they have been isolated.

Methods of Use: Drug Screening

This invention is particularly useful for screening compounds by using the ACTC polypeptide or binding fragment thereof in any of a variety of drug screening techniques.

The ACTC polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an ACTC polypeptide or fragment and the agent being tested, or examine the degree to which the formation of a complex between an ACTC polypeptide or fragment and a known ligand is interfered with by the agent being tested.

Thus, the present invention provides methods of screening for drugs comprising contacting such an agent with an ACTC polypeptide or fragment thereof and assaying (i) for the presence of a complex between the agent and the ACTC polypeptide or fragment, or (ii) for the presence of a complex between the ACTC polypeptide or fragment and a ligand, by methods well known in the art. In such competitive binding assays the ACTC polypeptide or fragment is typically labeled. Free ACTC polypeptide or fragment is separated from that present in a protein:protein complex, and the amount of free (i.e., uncomplexed) label is a measure of the binding of the agent being tested to ACTC or its interference with ACTC:ligand binding, respectively. One may also measure the amount of bound, rather than free, ACTC. It is also possible to label the ligand rather than the ACTC and to measure the amount of ligand binding to ACTC in the presence and in the absence of the drug being tested.

Another technique for drug screening provides high throughput screening for compounds having suitable binding affinity to the ACTC polypeptides and is described in detail in Geysen (published PCT application WO 84/03564). Briefly stated, large numbers of different small peptide test compounds are synthesized on a solid substrate, such as plastic pins or some other surface. The peptide test compounds are reacted with ACTC polypeptide and washed. Bound ACTC polypeptide is then detected by methods well known in the art.

Purified ACTC can be coated directly onto plates for use in the aforementioned drug screening techniques. However, non-neutralizing antibodies to the polypeptide can be used to capture antibodies to immobilize the ACTC polypeptide on the solid phase.

This invention also contemplates the use of competitive drug screening assays in which neutralizing antibodies capable of specifically binding the ACTC polypeptide compete with a test compound for binding to the ACTC polypeptide or fragments thereof. In this manner, the antibodies can be used to detect the presence of any peptide which shares one or more antigenic determinants of the ACTC polypeptide.

The above screening methods are not limited to assays employing only ACTC but are also applicable to studying ACTC-protein complexes, e.g., the complex which occurs between ACTC and myosin, actinin or dystrophin. The effect of drugs on the activity of this complex, especially when either the ACTC or the myosin, actinin or dystrophin binding protein contains a mutation, is analyzed.

In accordance with these methods, the following assays are examples of assays which can be used for screening for drug candidates.

A mutant ACTC (per se or as part of a fusion protein) is mixed with a wild-type protein (per se or as part of a fusion protein) to which wild-type ACTC binds. This mixing is performed in both the presence of a drug and the absence of the drug, and the amount of binding of the mutant ACTC with the wild-type protein is measured. If the amount of the binding is more in the presence of said drug than in the absence of said drug, the drug is a drug candidate for treating IDC resulting from a mutation in ACTC.

A wild-type ACTC (per se or as part of a fusion protein) is mixed with a wild-type protein (per se or as part of a fusion protein) to which wild-type ACTC binds. This mixing is performed in both the presence of a drug and the absence of the drug, and the amount of binding of the wild-type ACTC with the wild-type protein is measured. If the amount of the binding is more in the presence of said drug than in the absence of said drug, the drug is a drug candidate for treating IDC resulting from a mutation in ACTC.

A mutant protein, which as a wild-type protein binds to ACTC (per se or as part of a fusion protein) is mixed with a wild-type ACTC (per se or as part of a fusion protein). This mixing is performed in both the presence of a drug and the absence of the drug, and the amount of binding of the mutant protein with the wild-type ACTC is measured. If the amount of the binding is more in the presence of said drug than in the absence of said drug, the drug is a drug candidate for treating IDC resulting from a mutation in the gene encoding the protein.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an ACTC specific binding partner, such as myosin, actinin or dystrophin, or to find mimetics of the ACTC polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of IDC, use of such a substance in the manufacture of a composition for administration, e.g., for treatment of IDC, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Diagnosis and Diagnostic Kits

In order to detect the presence of an ACTC allele predisposing an individual to IDC, a biological sample such as blood is prepared and analyzed for the presence or absence of susceptibility alleles of ACTC. In order to detect the presence of IDC or as a prognostic indicator, a biological sample is prepared and analyzed for the presence or absence of mutant alleles of ACTC. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant ACTC sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences, the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 15 for ACTC. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; U.S. Pat. No. 4,868,105; and in EP 225,807A.

As noted above, non-PCR based screening assays are also contemplated in this invention. This procedure hybridizes a nucleic acid probe (or an analog such as a methyl phosphonate backbone replacing the normal phosphodiester) to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al., 1986.

Two-step label amplification methodologies are known in the art. These assays work on the principle that a small ligand (such as digoxigenin, biotin, or the like) is attached to a nucleic acid probe capable of specifically binding ACTC. Allele specific probes are also contemplated within the scope of this example and exemplary allele specific probes include probes encompassing the predisposing mutations of this disclosure.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting ACTC. Thus, in one example to detect the presence of ACTC in a cell sample, more than one probe complementary to the gene is employed and in particular the number of different probes is alternatively two, three, or five different nucleic acid probe sequences. In another example, to detect the presence of mutations in the ACTC gene sequence in a patient, more than one probe complementary to these genes is employed where the cocktail includes probes capable of binding to the allele-specific mutations identified in populations of patients with alterations in ACTC. In this embodiment, any number of probes can be used, and will preferably include probes corresponding to the major gene mutations identified as predisposing an individual to IDC.

Methods of Use: Peptide Diagnosis and Diagnostic Kits

The presence of IDC can also be detected on the basis of the alteration of wild-type ACTC polypeptide. Such alterations can be determined by sequence analysis in accordance with conventional techniques. More preferably, antibodies (polyclonal or monoclonal) are used to detect differences in, or the absence of ACTC peptides. Techniques for raising and purifying antibodies are well known in the art and any such techniques may be chosen to achieve the preparations claimed in this invention. In a preferred embodiment of the invention, antibodies will immunoprecipitate ACTC proteins from solution as well as react with these proteins on Western or immunoblots of polyacrylamide gels. In another preferred embodiment, antibodies will detect ACTC proteins in paraffin or frozen tissue sections, using immunocytochemical techniques.

Preferred embodiments relating to methods for detecting ACTC or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Alternatively, alterations in the ACTC sequence can be determined by detecting alterations in the interaction of ACTC with myosin, actinin and/or dystrophin. Wild-type myosin, actinin or dystrophin can be bound to a solid phase and the interaction with ACTC assayed by conventional techniques. Analogously, alterations in myosin, actinin or dystrophin which affect its interaction with ACTC can be detected using wild-type ACTC, or a fragment of ACTC which interacts with myosin, actinin or dystrophin, bound to a solid phase.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., ACTC polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., ACTC polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved ACTC polypeptide activity or stability or which act as inhibitors, agonists, antagonists, etc. of ACTC polypeptide activity. By virtue of the availability of cloned ACTC sequences, sufficient amounts of the ACTC polypeptide may be made available to perform such analytical studies as x-ray crystallography. In addition, the knowledge of the ACTC protein sequences provided herein will guide those employing computer modeling techniques in place of, or in addition to x-ray crystallography.

Methods of Use: Gene Therapy

According to the present invention, a method is also provided of supplying wild-type ACTC function to a cell which carries a mutant ACTC allele. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the ACTC gene or fragment, where applicable, may be employed in gene therapy methods in order to increase the amount of the expression products of such gene in cells. It may also be useful to increase the level of expression of the ACTC gene even in those persons in which the mutant gene is expressed at a "normal" level, but the gene product is not fully functional.

Gene therapy would be carried out according to generally accepted methods, for example, as described by Friedman (1991) or Culver (1996). Cells from a patient would be first analyzed by the diagnostic methods described above, to ascertain the production of ACTC polypeptide in the cells. A virus or plasmid vector (see further details below), containing a copy of the ACTC gene linked to expression control elements, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and published PCT application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for preparing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993) and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al., 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991).

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes ACTC, expression will produce ACTC. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to heart tissue are preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry an ACTC susceptibility allele are treated with a gene delivery vehicle such that some or all of their heart precursor cells receive at least one additional copy of a functional normal ACTC allele. In this step, the treated individuals have reduced risk of IDC to the extent that the effect of the susceptible allele has been countered by the presence of the normal allele.

Methods of Use: Peptide Therapy

Peptides which have ACTC activity can be supplied to cells which carry a mutant or missing ACTC allele. Protein can be produced by expression of the cDNA sequence in bacteria, for example, using known expression vectors. Alternatively, ACTC polypeptide can be extracted from ACTC-producing mammalian cells. In addition, the techniques of synthetic chemistry can be employed to synthesize ACTC protein. Any of such techniques can provide the preparation of the present invention which comprises the ACTC protein. The preparation is substantially free of other human proteins. This is most readily accomplished by synthesis in a microorganism or in vitro.

Active ACTC molecules can be introduced into cells by microinjection or by use of liposomes, for example. Alternatively, some active molecules may be taken up by cells, actively or by diffusion. Supply of molecules with ACTC activity should lead to partial reversal of IDC. Other molecules with ACTC activity (for example, peptides, drugs or organic compounds) may also be used to effect such a reversal. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant ACTC alleles, usually from a second animal species, as well as insertion of disrupted homologous genes. Alternatively, the endogenous ACTC gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the presence of IDC must be assessed. If the test substance prevents or suppresses the appearance of IDC, then the test substance is a candidate therapeutic agent for treatment of IDC. These animal models provide an extremely important testing vehicle for potential therapeutic products.

The identification of the association between the ACTC gene mutations and IDC permits the early presymptomatic screening of individuals to identify those at risk for developing IDC. To identify such individuals, ACTC alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal ACTC gene or appropriate fragment (coding sequence or genomic sequence) are determined and then compared, or (2) the RNA transcripts of the ACTC gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the ACTC gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal ACTC gene.

Alternatively, polymerase chain reactions (PCRs) are performed with primer pairs for the 5' region or the exons of the ACTC gene. PCRs can also be performed with primer pairs based on any sequence of the normal ACTC gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common ACTC gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal ACTC gene and defective genes. This comparison is performed in steps using small (~500 bp) restriction fragments of the ACTC gene as the probe. First, the ACTC gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the ACTC gene fragments are transcribed in vitro using the SP6 transcription system, well known in the art, in the presence of [α-$^{32}$P]GTP, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the ACTC fragment and the ACTC allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the ACTC gene and the consequent presence of IDC. These variants can take a number of forms. The most severe forms would be frame shift mutations or large deletions which would cause the gene to code for an abnormal protein or one which would significantly alter protein expression. Less severe disruptive mutations would include small in-frame deletions and non-conservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Pharmaceutical Compositions and Routes of Administration

The ACTC polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated.

Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

EXAMPLES

The present invention is further detailed in the following Examples, which are offered by way of illustration and are not intended to limit the invention in any manner. Standard techniques well known in the art or the techniques specifically described below are utilized.

Example 1

IDC Families

Two unrelated families with autosomal dominant IDC were studied. One family is of German ancestry and the other is of Swedish-Norwegian ancestry (see FIGS. 1A–1B). The family members were phenotypically characterized by echocardiography (Michels et al., 1992). Echocardiograms and blood samples for DNA analyses were obtained from participating family members after informed, written consent. IDC was defined as left ventricular (LV) end-diastolic dimension >95th percentile for age and body surface area, and shortening fraction <28%. The following formulas were used: body surface area $(m^2)=0.007184 \times$ height $(cm)^{0.725} \times$ weight $(kg)^{0.425}$ (Du Bois and Du Bois, 1916); 95th percentile for left ventricular end-diastolic dimension (mm)=45.3 $(BSA)^{1/3}$–0.03 (age)–7.2+12% (Henry et al., 1980); shortening fraction (%)=100×(left ventricular end-diastolic dimension−left ventricular end-systolic dimension)÷left ventricular end–diastolic dimension.

Figure 2:
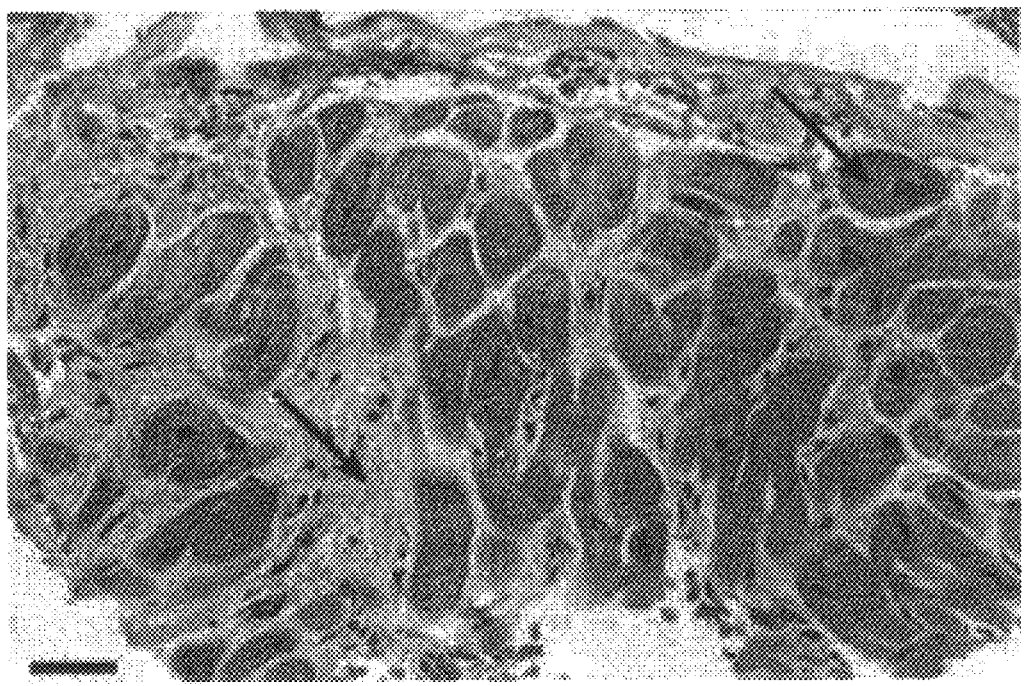
FIG. 2. Photomicrograph from right ventricle biopsy specimen of individual II.3 in K-9695 demonstrates moderate focal interstitial fibrosis (left arrow) and myocyte hypertrophy (right arrow). There is no evidence of myofibrillar disarray, as seen in hypertrophic cardiomyopathy, or myocarditis. Histopathologic findings were similar but less severe for individual II.3 in K-1453 (data not shown). The specimen was stained with hematoxylin and eosin. Scale bar, 50 μm.

The results of phenotypic evaluation are shown in Table 2. Individuals in both families had variable age at diagnosis (1 to 41 years), similar to other IDC families, with age at diagnosis differing by as much as 20 to 50 years (Olson and Keating, 1997; Bowles et al., 1996; Michels et al., 1985; Olson and Keating, 1996). Heart biopsy specimens from the proband of each family revealed histopathologic findings consistent with IDC (FIG. 2). Neither family had phenotypic features of hypertrophic cardiomyopathy. Hypertrophy of the heart was not evident on electrocardiograms or echocardiograms. Myofibrillar disarray, which is characteristic of hypertrophic cardiomyopathy, was absent on histopathologic examination of cardiac biopsy specimens.

Example 2

Identification of Mutations in ACTC in IDC Families

Actin is essential for normal structure and function of cardiac myocytes. During development, 5 of the 6 actin isoforms encoded by separate genes are expressed in myocytes. In mature cardiac myocytes, however, only cardiac and skeletal actin are expressed, and cardiac actin is the major isoform (~80%) (Herman, 1993; Lu et al., 1992; Gimona et al., 1994; Vandekerckhove et al., 1986). To test the hypothesis that actin dysfunction leads to heart failure, we investigated the cardiac actin gene (ACTC) on chromosome 15q14 as a candidate for IDC. Oligonucleotide primers complementary to flanking intron sequence were developed for the six exons of ACTC. Primers were designed using the published genomic DNA sequence for ACTC (Hamada et al., 1982) and OLIGO® 4.03 Primer Analysis Software (National Biosciences, Inc., Plymouth, Minn.). The published ACTC coding sequence is shown as SEQ ID NO: 1 and the encoded protein as SEQ ID NO: 2 in the SEQUENCE LISTING. For intron sequence see Hamada et al., 1982 and also see GenBank Accession Nos. J00070, J00071, J00072 and J00073

TABLE 2

| Pedigree | Age (years) | BSA ($m^2$) | LV end-diastolic dimension (mm) | Shortening fraction (%) | Phenotypic assignment | Cardiac actin genotype |
|---|---|---|---|---|---|---|
| K-1453 | | | | | | |
| II.1 | 39 | 1.96 | 51 (54) | 35 | Normal | Normal |
| II.4 | 36 | 1.53 | 59 (49) | 20 | IDC | Arg312His |
| III.1 | 15 | 1.84 | 53 (54) | 36 | Uncertain | Arg312His |
| III.2 | 5 | 0.74 | 48 (38) | 13 | IDC | Arg312His |
| III.3 | 2 | 0.62 | 37 (35) | 27 | IDC | Arg312His |
| K-9695 | | | | | | |
| II.1 | 42 | 1.81 | 51 (52) | 35 | Normal | Normal |
| II.3 | 41 | 1.85 | 58 (53) | 7 | IDC | Glu361Gly |
| II.5 | 38 | 1.65 | 49 (51) | 43 | Normal | Normal |
| II.6 | 34 | 1.54 | 51 (49) | 31 | LV dilation | Glu361Gly |
| III.2 | 16 | 1.61 | 45 (51) | 38 | Uncertain | Normal |
| III.3 | 14 | 1.38 | 51 (48) | 22 | ICD | Glu361Gly |
| III.1 | 9 | 1.05 | 43 (43) | 37 | Borderline LV dilation | Glu361Gly |

The 95th percentiles for LV end-diastolic dimension, based on body surface area and age, are indicated in parentheses.
Normal shortening fraction is ≦28%. Abnormal values are indicated in bold type.
Individuals <20 years of age with normal values were classified as uncertain, based on ~5–10% disease penetrance in this age group (Mestroni et al., 1994).
Phenotypic data were obtained before DNA analyses.
BSA - body surface are
LV - left ventricle which are all incorporated herein by reference. The forward primer for exon 5 overlaps 5 bp of coding sequence to avoid a repetitive dinucleotide sequence near the intron-exon boundary. Primer sequences are as follows:

exon 1F: 5'-CCCCTGAAGCTGTGCCAAGA-3' (SEQ ID NO: 3)

exon 1R: 5'-GGCTCGGCGGGAAGTTTAC-3' (SEQ ID NO: 4)

exon 2F: 5'-TAAATGGACAAGACACTGATTAT-3' (SEQ ID NO: 5)

exon 2R: 5'-CAGCAAGGTCGGTGACTT-3' (SEQ ID NO: 6)

exon 3F: 5'-GCTAGAGCAGTGGTGTTGTC-3' (SEQ ID NO: 7)

exon 3R: 5'-AGGTAGGCGGATTCAGTG-3' (SEQ ID NO: 8)

exon 4F: 5'-CTCACTGAATCCGCCTACCT-3' (SEQ ID NO: 9)

exon 4R: 5'-CTACACCAGACCCTACAACTC-3' (SEQ ID NO: 10)

exon 5F: 5'-GACTCGTTCCCAGGTATG-3' (SEQ ID NO: 11)

exon 5R: 5'-GATCTCCCACTCACAAAAG-3' (SEQ ID NO: 12)

exon 6F: 5'-AAGTTTTTGTTTTCTTCTGC-3' (SEQ ID NO: 13)

exon 6R: 5'-CATAATACCGTCATCCTGA-3' (SEQ ID NO: 14)

PCR product sizes for exons 1 to 6 are 167 bp, 457 bp, 292 bp, 291 bp, 222 bp and 214 bp, respectively. PCR was performed with 25 ng genomic DNA, 10 mM Tris-HCl (pH 8.3), 50 mM KCl, 1.5 mM MgCl$_2$, 200 µM dGTP, 200 µM dATP, 200 µM dCTP, 0.5 µM forward primer, 0.5 µM reverse primer, 10% glycerol, 0.05 units Taq DNA polymerase and 1 µCi [α-$^{32}$P]dCTP in a final volume of 10 µL. Amplification conditions were 94° C. for 5 minutes, followed by 30 cycles of 94° C. for 30 seconds, 52 to 60° C. for 30 seconds, and 72° C. for 30 seconds followed by 72° C. for 10 minutes using a Perkin-Elmer Cetus 9600 thermocycler. For exon 2, 10 µL of PCR product was digested with Bgl II, resulting in 198-bp and 259-bp fragments.

Single-strand conformation polymorphism (SSCP) analyses were performed on these PCR products (Orita et al., 1989). Reactions were diluted with 25 µL of 0.1% SDS and 10 mM EDTA and 25 µL of 95% formamide dye. Diluted samples were denatured at 94° C. for 10 minutes, and 3 µL samples were subjected to gel electrophoresis under three conditions: 0.5× and 1× Mutation Detection Enhancement™ gels (FMC Bioproducts, Rockland, Me.) at 800 volts for 14 to 30 hours (room temperature) and 10% nondenaturing polyacrylamide (49:1 polyacrylamide:bisacrylamide) with 10% glycerol at 30 watts for 4 to 6 hours (4° C.). Gels were then dried for autoradiography.

SSCP analyses of ACTC in kindred 1453 (K-1453) identified an anomalous conformer for exon 5 that cosegregated with IDC (data not shown). Sequencing of the conformer revealed a G-to-A substitution in codon 312 (Arg312His) of SEQ ID NO: 15 (FIG. 1A). This alteration was confirmed by testing for a new Bcl I restriction site. It was inherited by three individuals with IDC (ages 36, 5 and 2) and a 15-year-old who has not developed IDC.

The sequencing of the conformers was performed as follows. Normal and anomalous single-strand conformers were cut from dried gels and eluted in 100 µL of water at 65° C. for 30 minutes. The eluted DNA (10 µL) was used as a template for a second PCR using the original primer pair. Products were fractionated in 1% agarose gels and DNA was purified by phenol and chloroform extraction. Forward and reverse [α-$^{33}$P]ddNTP cycle sequencing was performed using a Thermo Sequenase™ kit (Amersham Life Sciences, Inc., Cleveland). Mutations were confirmed by PCR amplifications and cycle sequencing of genomic DNA.

Figure 1B:
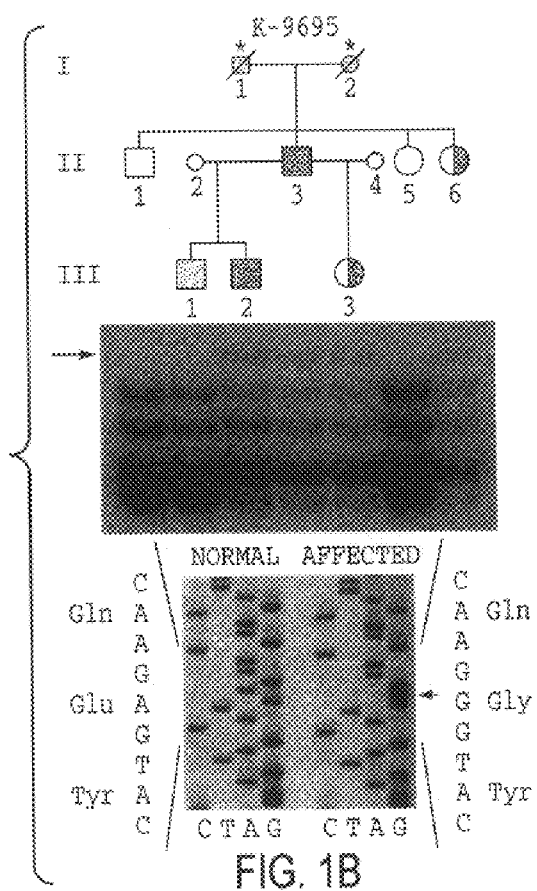

Analysis of kindred 9695 (K-9695) revealed an anomalous conformer for ACTC exon 6 that cosegregated with IDC (FIG. 1B). DNA sequence analysis demonstrated an A-to-G substitution in codon 361 (Glu361Gly) of SEQ ID NO: 15. This alteration was inherited by two individuals with IDC (ages 41 and 14) in addition to a 34-year-old with a dilated heart and a 9-year-old with borderline heart size.

No additional mutations were identified in other exons of ACTC for either family. To eliminate the possibility that these substitutions were polymorphisms within the normal population, 435 unrelated control individuals (870 chromosomes) were tested. No anomalous SSCP conformers were identified for ACTC exons 5 or 6 in these controls. In addition, sequence comparisons revealed that both substitutions affect amino acids that are invariant in all human actin isoforms and actin in mice, Drosophila, yeast and rice (data not shown, comparison of actin sequences was made using the combined protein database and the NCBI BLAST Web Site, http://www.ncbi.nlm.nih.gov/cgi-bin/BLAST/nph-blast?form=1). Arg312His and Glu361Gly substitutions have not been evaluated in functional studies of mutant actin. However, an Arg312Ala substitution causes reduced viability of haploid yeast (Arg312Ala) (Hennessey et al., 1993). Thus, the ACTC variants described here are IDC-associated mutations rather than rare polymorphisms.

Example 3

Generation of Polyclonal Antibody against ACTC

Segments of ACTC coding sequence are expressed as fusion protein in *E. coli*. The overexpressed protein is purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of ACTC coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the ACTC fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against the mutant forms of the ACTC gene product. These antibodies, in conjunction with antibodies to wild type ACTC, are used to detect the presence and the relative level of the mutant forms in various tissues and biological fluids.

Example 4

Generation of Polyclonal Antibody
Against ACTC:ACTC-Binding Protein Complex

ACTC is capable of binding to certain proteins, e.g., myosin, actinin and dystrophin. A complex of at least two proteins is prepared, e.g., by mixing purified preparations of each of ACTC and one of the ACTC-binding proteins. If desired, the protein complex can be stabilized by cross-linking the proteins in the complex by methods known to those of skill in the art. The protein complex is used to immunize rabbits and mice using a procedure similar to the one described by Harlow and Lane, 1988. This procedure has been shown to generate Abs against various other proteins (for example, see Kraemer et al., 1993).

Briefly, the purified protein complex is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure is repeated to generate antibodies against forms of the complex which comprise mutant ACTC or mutant ACTC-binding protein (e.g., myosin, actinin or dystrophin). These antibodies, in conjunction with antibodies to wild type ACTC or ACTC-binding protein (e.g., myosin, actinin or dystrophin), are used to detect the presence and the relative level of the mutant forms in various tissues and biological fluids.

Example 5

Generation of Monoclonal Antibodies Specific for ACTC

Monoclonal antibodies are generated according to the following protocol. Mice are immunized with immunogen comprising intact ACTC or ACTC peptides (wild type or mutant) conjugated to keyhole limpet hemocyanin using glutaraldehyde or EDC as is well known.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of ACTC specific antibodies by ELISA or RIA using wild type or mutant ACTC target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Example 6

Generation of Monoclonal Antibodies Specific for ACTC:ACTC-Binding Protein Complex Monoclonal antibodies are generated according to the following protocol. Mice are immunized with immunogen comprising ACTC:ACTC-binding protein complexes (wild type or mutant), wherein the ACTC-binding protein is, e.g., myosin, actinin or dystrophin, conjugated to keyhole limpet hemocyanin using glutaraldehyde or EDC as is well known. The complexes may be stabilized by cross-linking.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of ACTC:ACTC-binding protein complex specific antibodies by ELISA or RIA using wild type or mutant ACTC:ACTC-binding protein complexes as target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development. Antibodies are tested for binding to ACTC alone or to ACTC-binding protein alone to determine which are specific for the complex as opposed to binding to the individual proteins.

Example 7

Sandwich Assay for ACTC

Monoclonal antibody is attached to a solid surface such as a plate, tube, bead or particle. Preferably, the antibody is attached to the well surface of a 96-well ELISA plate. 100 μL sample (e.g., serum, urine, tissue cytosol) containing the ACTC peptide/protein (wild-type or mutants) is added to the solid phase antibody. The sample is incubated for 2 hrs at room temperature. Next the sample fluid is decanted, and the solid phase is washed with buffer to remove unbound material. 100 μL of a second monoclonal antibody (to a different determinant on the ACTC peptide/protein) is added to the solid phase. This antibody is labeled with a detector molecule (e.g., $^{125}I$, enzyme, fluorophore, or a chromophore) and the solid phase with the second antibody is incubated for two hours at room temperature. The second antibody is decanted and the solid phase is washed with buffer to remove unbound material.

The amount of bound label, which is proportional to the amount of ACTC peptide/protein present in the sample, is quantified. Separate assays are performed using monoclonal antibodies which are specific for the wild-type ACTC as well as monoclonal antibodies specific for each of the mutations identified in ACTC.

Example 8

Drug Screening

The invention is useful in screening for drugs which can overcome mutations in ACTC and also mutations in myosin, actinin or dystrophin which may cause IDC. The knowledge that ACTC binds to myosin, actinin and dystrophin is useful in designing such assays. If a mutation is present in either ACTC or in one of myosin, actinin or dystrophin which prevents ACTC from binding to myosin, actinin or dystrophin, drugs may be screened which will overcome the mutation and allow the protein binding to occur and result in an active complex. Such screening assays can be, e.g., a yeast two hybrid assay which is dependent upon two proteins interacting. In such an assay, the presence of a mutant protein may show no activity or low activity in such an assay, while the presence of a useful drug will result in formation of a proper complex which results in activity in the assay.

A simple binding assay which shows the binding, i.e., formation of a complex, can similarly be used as outlined above. Useful drugs will increase the formation of ACTC:ACTC-binding protein complexes. Antibodies may also be used to monitor the amount of complex present. Antibodies specific for the complex are especially useful. If the presence of a drug increases the amount of complex present, then the drug is a good candidate for treating the IDC which is a result of the mutation in either ACTC or an ACTC-binding protein.

While the invention has been disclosed in this patent application by reference to the details of preferred embodiments of the invention, it is to be understood that the disclosure is intended in an illustrative rather than in a limiting sense as it is contemplated that modifications will readily occur to those skilled in the art, within the spirit of the invention and the scope of the appended claims.

LIST OF REFERENCES

Abraham W T and Bristow M R (1997). *Circulation* 96:2755–2757.
Altschul S F, et al. (1997). *Nucl. Acids Res.* 25:3389–3402.
Anand R (1992). *Techniques for the Analysis of Complex Genomes*, (Academic Press).
Anderson W F, et al. (1980). *Proc. Natl. Acad. Sci. USA* 77:5399–5403.
Ausubel F M, et al. (1992). *Current Protocols in Molecular Biology*, (J. Wiley and Sons, N.Y.)
Bandyopadhyay P K and Temin H M (1984). *Mol. Cell. Biol.* 4:749–754.
Bartel P L, et al. (1993). "Using the 2-hybrid system to detect protein-protein interactions." In *Cellular Interactions in Development: A Practical Approach*, Oxford University Press, pp. 153–179.
Beaucage S L and Caruthers M H (1981). *Tetra. Letts.* 22:1859–1862.
Berglund P, et al. (1993). *Biotechnology* 11:916–920.
Berkner K L, et al. (1988). *BioTechniques* 6:616–629.
Berkner K L (1992). *Curr. Top. Microbiol. Immunol.* 158:39–66.
Borman S (1996). *Chemical & Engineering News*, December 9 issue, pp. 42–43.
Bowles K R, Gajarski R, Porter P, Goytia V, Bachinski L, Roberts R, Pignatelli R and Towbin J A (1996). *J. Clin. Invest.* 98:1355–1360.
Breakefield X O and Geller A I (1987). *Mol. Neurobiol.* 1:339–371.
Brinster R L, et al. (1981). *Cell* 27:223–231.
Buchschacher G L and Panganiban A T (1992). *J. Virol.* 66:2731–2739.
Capecchi M R (1989). *Science* 244:1288.
Cariello N F (1988). *Am. J. Human Genetics* 42:726–734.
Chee M, et al. (1996). *Science* 274:610–614.
Chevray P M and Nathans D N (1992). *Proc. Natl. Acad Sci. USA* 89:5789–5793.
Compton J (1991). *Nature* 350:91–92.
Conner B J, et al. (1983). *Proc. Natl. Acad. Sci. USA* 80:278–282.
Costantini F and Lacy E (1981). *Nature* 294:92–94.
Cotton M, Langle-Rouault F, Kirlappos H, Wagner E, Mechtler K, Zenke M, Beug H and Birnstiel M L (1990). *Proc. Natl. Acad. Sci. USA* 87:4033–4037.
Cotton R G, Rodrigues N R and Campbell R D (1988). *Proc. Natl. Acad. Sci. USA* 85:4397–4401.
Culver K (1996). *Gene Therapy: A Primer for Physicians*, 2nd Ed., Mary Ann Liebert.
Curiel D T, et al. (1992). *Hum. Gene Ther.* 3:147–154.
Curiel D T, et al. (1991). *Proc. Natl. Acad. Sci. USA* 88:8850–8854.
Dec G W and Fuster V (1994). *N. Engl. J. Med.* 331:1564–1575.
DeRisi J, Penland L, Brown P O, Bittner M L, Meltzer P S, Ray M, Chen Y, Su Y A and Trent J M (1996). *Nat. Genet.* 14:457–460.
Deutscher M (1990). *Meth. Enzymology* 182 (Academic Press, San Diego, Calif.).
Donehower L A, et al. (1992). *Nature* 356:215.
Du Bois D and Du Bois E F (1916). *Arch. Intern. Mel.* 17:863.
Editorial (1996). *Nature Genetics* 14:367–370.
Elghanian R, et al. (1997). *Science* 277:1078–1081.
*Enhancers and Eukaryotic Gene Expression*, Cold Spring Harbor Press, Cold Spring Harbor, N.Y. (1983).
Erickson J, et al. (1990). *Science* 249:527–533.
Fahy E, Kwoh D Y and Gingeras T R (1991). *PCR Methods Appl.* 1:25–33.
Felgner P L, et al. (1987). *Proc. Natl. Acad. Sci. USA* 84:7413–7417.
Fields S and Song O -K (1989). *Nature* 340:245–246.
Fiers W, et al. (1978). *Nature* 273:113–120.
Fink D J, et al. (1 992). *Hum. Gene Ther.* 3:11–19.
Fink D J et al. (1996). *Ann. Rev. Neurosci.* 19:265–287.
Finkelstein J, et al. (1990). *Genomics* 7:167–172.
Fodor S P A (1997). *Science* 277:393–395.
Freese A, et al. (1990). *Biochem. Pharmacol.* 40:2189–2199.
Friedman T (1991). In *Therapy for Genetic Diseases*, T. Friedman, ed., Oxford University Press, pp. 105–121.
Gimona M, Vandekerckhove J, Goethals M, Herzog M, Lando Z and Small J V (1994). *Cell Motil. Cytoskeleton* 27:108–116.
Glover D (1985). *DNA Cloning*, I and II (Oxford Press).
Goding (1986). *Monoclonal Antibodies: Principles and Practice*, 2d ed. (Academic Press, N.Y.).
Godowski P J, et al. (1988). *Science* 241:812–816.
Gordon J W, et al. (1980). *Proc. Natl. Acad. Sci. USA* 77:7380–7384.
Gorziglia M and Kapikian A Z (1992). *J. Virol.* 66:4407–4412.
Graham F L and van der Eb A J (1973). *Virology* 52:456–467.
Gregorio C C (1997). *Cell Struct. Funct.* 22:191–195.
Grompe M (1993). *Nature Genetics* 5:111–117.
Grompe M, et al. (1989). *Proc. Natl. Acad. Sci. USA* 86:5855–5892.
Guthrie G and Fink G R (1991). *Guide to Yeast Genetics and Molecular Biology* (Academic Press).
Hacia J G, et al. (1996). *Nature Genetics* 14:441–447.
Hamada H, Petrino M G and Kakunaga T (1982). *Proc. Natl. Acad. Sci. USA* 79:5901–5905.
Harlow E and Lane D (1988). *Antibodies: A Laboratory Manual* (Cold Spring Harbor Laboratory, Cold Spring Harbor, N.Y.).
Hasty P K, et al. (1991). *Nature* 350:243.
Helseth E, et al. (1990). *J. Virol.* 64:2416–2420.
Hennessey E S, Drummond D R and Sparrow J C (1993). *Biochem. J.* 291:657–671.
Henry W L, Gardin J M and Ware J H (1980). *Circulation* 62:1054–1061.
Herman I M (1993). *Curr. Opin. Cell. Biol.* 5:48–55.

Hodgson J (1991). *Bio/Technology* 9:19–21.
Holmes K C, Popp D, Gebhard W and Kabsch W (1990). *Nature* 347:44–49.
Huse W D, et al. (1989). *Science* 246:1275–1281.
Innis M A, et al. (1990). *PCR Protocols: A Guide to Methods and Applications* (Academic Press, San Diego, Calif.).
Jablonski E, et al. (1986). *Nucl. Acids Res.* 14:6115–6128.
Jakoby W B and Pastan I H (eds.) (1979). "Cell Culture." *Methods in Enzymology,* volume 58 (Academic Press, Inc., Harcourt Brace Jovanovich (New York)).
Johnson P A, et al. (1992). *J. Virol.* 66:2952–2965.
Johnson, et al. (1993). "Peptide Turn Mimetics" in *Biotechnology and Pharmacy,* Pezzuto et al., eds., Chapman and Hall, New York.
Kaneda Y, et al. (1989). *J. Biol. Chem.* 264:12126–12129.
Kanehisa M (1984). *Nucl. Acids Res.* 12:203–213.
Kasper E K, Agema W R, Hutchins G M, Deckers J W, Hare J M and Baughman K L (1994). *J. Am. Coll. Cardiol.* 23:586–590.
Kinszler K W, et al. (1991). *Science* 251:1366–1370.
Kohler G and Milstein C (1975). *Nature* 256:495–497.
Kraemer F B, et al. (1993). *J. Lipid Res.* 34:663–672.
Kubo T, et al. (1988). *FEBS Letts.* 241:119.
Kuhlman P A, Hemmings L and Critchley D R (1992). *FEBS Lett.* 304:201–206.
Kumar A, Crawford K, Close L, Madison M, Lorenz J, Doetschman T, Pawlowski S, Duffy J, Neumann J, Robbins J, Boivin GP, O'Toole B A and Lessard J L (1997). *Proc. Natl. Acad. Sci. USA* 94:4406–4411.
Kyte J and Doolittle R F (1982). *J. Mol. Bio.* 157:105–132.
Landegren U, et al. (1988). *Science* 242:229–237.
Lankford E B, Epstein N D, Fananapazir L and Sweeney H L (1995). *J. Clin. Invest.* 95:1409–1414.
Lee J E, et al. (1995). *Science* 268:836–844.
Levine B A, Moir A J, Patchell V B and Perry S V (1992). *FEBS Lett.* 298:44–48.
Lim C S, et al. (1991). *Circulation* 83:2007–2011.
Lipshutz R J, et al. (1995). *Biotechniques* 19:442–447.
Lockhart D J, et al. (1996). *Nature Biotechnology* 14:1675–1680.
Lu M H, DiLullo C, Schultheiss T, Holtzer S, Murray J M, Choi J, Fischman D A and Holtzer H (1992). *J. Cell Biol.* 117:1007–1022.
Madzak C, et al. (1992). *J. Gen. Virol.* 73:1533–1536.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401–407.
Manolio T A, Baughman K L, Rodeheffer R, Pearson T A, Bristow J D, Michels V V, Abelmann W H and Harlan W R (1992). *Am J. Cardiol.* 69:145 8–1466.
Margolskee R F (1992). *Curr. Top. Microbiol. Immunol.* 158:67–95.
Martin R, et al. (1990). *BioTechniques* 9:762–768.
Matteucci M D and Caruthers M H (1981). *J. Am. Chem. Soc.* 103:3185.
Matthews J A and Kricka U J (1988). *Anal. Biochem.* 169:1–25.
Mendelian Inheritance in Man, #s 102540, 115200, 302045, 600884, 601154, 601493, 601494.
Merrifield B (1963). *J. Am. Chem. Soc.* 85:2149–2156.
Mestroni L, Krajinovic M, Severini GM, Pinamonti B, Di Leniarda A, Giacca M, Falaschi A and Camerini F (1994). *Br. Heart J.* 72:S35–S41.
Metzger D, et al. (1988). *Nature* 334:31–36.
Michels V V, Driscoll D J and Miller F A (1985). *Am. J. Cardiol.* 55:1232–1233.
Michels V V, Moll P P, Miller F A, Tajik A J, Chu J S, Driscoll D J, Burnett J C, Rodeheffer R J, Chesebro J H and Tazelaar H D (1992). *N. Engl. J. Med.* 326:77–82.
Miller A D (1992). *Curr. Top. Microbiol. Immunol.* 158:1–24.
Miller A D, et al. (1985). *Mol. Cell. Biol.* 5:431–437.
Miller A D, etal. (1988). *J. Virol.* 62:4337–4345.
Modrich P (1991). *Ann. Rev. Genet.* 25:229–253.
Mombaerts P, et al. (1992). *Cell* 68:869.
Moss B (1992). *Curr. Top. Microbiol. Immunol.* 158:25–38.
Moss B (1996). *Proc. Natl. Acad. Sci. USA* 93:11341–11348.
Muzyczka N (1992). *Curr. Top. Microbiol. Immunol.* 158:97–129.
Nabel E G, et al. (1990). *Science* 249:1285–1288.
Nabel (1992). *Hum. Gene Ther.* 3:399–410.
Naldini L et al. (1996). *Science* 272:263–267.
Newton C R, Graham A, Heptinstall L E, Powell S J, Summers C, Kalsheker N, Smith J C, and Markham A F (1989). *Nucl. Acids Res.* 17:2503–2516.
Nguyen Q, et al. (1992). *BioTechniques* 13:116–123.
Novack D F, et al. (1986). *Proc. Natl. Acad. Sc. USA* 83:586–590.
Ohi S, et al. (1990). *Gene* 89:279–282.
Olson T M and Keating M T (1996). *J. Clin. Invest.* 97:528–532.
Olson T M and Keating M T (1997). *Trends Cardiovasc. Med.* 7:60.
Orita M, Iwahana H, Kanazawa H, Hayashi K and Sekiya T (1989). *Proc. Natl. Acad. Sci. USA* 86:2766–2770.
Ortiz-Lopez R, Li H, Su J, Goytia V and Towbin J A (1997). *Circulation* 95:2434–2440.
Page K A, et al. (1990). *J. Virol.* 64:5270–5276.
Pellicer A, et al. (1980). *Science* 209:1414–1422.
Petropoulos C J, et al. (1992). *J. Virol.* 66:3391–3397.
Philpott K L, et al. (1992). *Science* 256:1448.
Quantin B, et al. (1992). *Proc. Natl. Acad. Sci. USA* 89:2581–2584.
Reisler E (1993). *Curr. Opin. Cell Biol.* 5:41–47.
*Remington's Pharmaceutical Sciences,* 18th Ed. (1990, Mack Publishing Co., Easton, Pa.).
Rigby P W J, et al. (1977). *J. Mol. Biol.* 113 :237–251.
Rosenfeld M A, et al. (1992). *Cell* 68:143–155.
Ruano G and Kidd K K (1989). *Nucl. Acids Res.* 17:8392.
Russell D and Hirata R (1998). *Nature Genetics* 18:323–328.
Sambrook J, et al. (1989). *Molecular Cloning: A laboratory Manual 2nd Ed.* (Cold Spring Harbor Laboratory, Cold Spring Harbor, N.Y.).
Scharf S J, et al. (1986). *Science* 233:1076–1078.
Schneider G, et al. (1998). *Nature Genetics* 18:180–183.
Scopes R (1982). *Protein Purification: Principles and Practice,* (Springer-Verlag, N.Y.).
Sheffield V C, et al. (1989). *Proc. Natl. Acad Sci. USA* 86:232–236.
Sheffield V C, et al., (1991). *Am. J. Hum. Genet.* 49:699–706.
Shenk T E, Rhodes C, Rigby P W and Berg P (1975). *Proc. Natl. Acad. Sci. USA* 72:989–993.
Shimada T, et al. (1991). *J. Clin. Invest.* 88:1043–1047.
Shinkai Y, et al. (1992). *Cell* 68:855.
Shoemaker D D, et al. (1996). *Nature Genetics* 14:450–456.
Snouwaert J N, et al. (1992). *Science* 257:1083.
Sorge J, et al. (1984). *Mol. Cell. Biol.* 4:1730–1737.
Spargo C A, Fraiser M S, van Cleve M, Wright D J, Nycz C M, Spears P A and Walker G T (1996). *Mol. Cell. Probes* 10:247–256.

Spirito P, Seidman C E, McKenna W J and Maron B J (1997). *N. Engl. J. Med.* 336:775–785.
Stewart M J, et al. (1992). *Hum. Gene Ther.* 3:267–275.
Stratford-Perricaudet L D, et al. (1990). *Hum. Gene Ther.* 1:241–256.
Valancius V and Smithies 0 (1991). *Mol. Cell Biol.* 11:1402.
Vandekerckhove J, Bugaisky G and Buckingham M (1986). *J. Biol. Chem.* 261:1838–1843.
Wagner E, et al. (1991). *Proc. Natl. Acad. Sci. USA* 88:4255–4259.
Wagner E, et al. (1990). *Proc. Natl. Acad. Sci. USA* 87:3410–3414.
Walker G T, Fraiser M S, Schram J L, Little M C, Nadeau J G and Malinowski D P (1992). *Nucl. Acids Res.* 20:1691–1696.
Wang C Y and Huang L (1989). *Biochemistry* 28:9508–9514.
Wartell R M, et al. (1990). *Nucl. Acids Res.* 18:2699–2705.
Watkins H, Seidman C E, Seidman J G, Feng H S and Sweeney H L (1996). *J. Clin. Invest.* 98:2456–2461.
Wells J A (1991). *Methods in Enzymol.* 202:390–411.
Wetmur J G and Davidson N (1968). *J. Mol. Biol.* 31:349–370.
White M B, et al. (1992). *Genomics* 12:301–306.
White R and Lalouel J M (1988). *Ann. Rev. Genet.* 22:259–279.
Wilkinson G W and Akrigg A (1992). *Nucleic Acids Res.* 20:2233–2239.
Wolff J A, et al. (1990). *Science* 247:1465–1468.
Wolff J A, et al. (1991). *BioTechniques* 11:474–485.
Wu D Y and Wallace R B (1989a). *Genomics* 4:560–569.
Wu C H, et al. (1989b). *J. Biol. Chem.* 264:16985–16987.
Wu G Y, et al. (1991). *J. Biol. Chem.* 266:14338–14342.
Zenke M, et al. (1990). *Proc. Natl. Acad. Sci. USA* 87:3655–3659.
Patents and Patent Applications:
EP 0332435
EP 225,807A
EP 425,731 A
Hitzeman et al., EP 73,675A.
WO 84/03564
WO 90/07936
WO 92/19195
WO 93/07282
WO 94/25503
WO 95/01203
WO 95/05452
WO 96/02286
WO 96/02646
WO 96/11698
WO 96/40871
WO 96/40959
WO 97/02048
WO 97/12635
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,554,101
U.S. Pat. No. 4,683,195
U.S. Pat. No. 4,683,202
U.S. Pat. No. 4,816,567
U.S. Pat. No. 4,868,105
U.S. Pat. No. 5,252,479
U.S. Pat. No. 5,270,184
U.S. Pat. No. 5,409,818
U.S. Pat. No. 5,436,146
U.S. Pat. No. 5,455,166
U.S. Pat. No. 5,550,050
U.S. Pat. No. 5,691,198
U.S. Pat. No. 5,747,469
U.S. Pat. No. 5,753,500

What is claimed is:

1. An isolated nucleic acid or complement of said nucleic acid or corresponding RNA wherein said nucleic acid encodes a protein of SEQ ID NO: 2 wherein said protein has a His rather than an Arg at position 314 or wherein said protein has a Gly rather than a Glu at position 363.

2. The isolated nucleic acid of claim 1 wherein said nucleic acid is SEQ ID NO: 1 wherein base number 941 is an A rather than a G or wherein base number 1088 is a G rather than an A.

3. An isolated nucleic acid or complement of said nucleic acid or corresponding RNA wherein said nucleic acid encodes a protein of SEQ ID NO: 16 wherein said protein has a His rather than an Arg at position 312 or wherein said protein has a Gly rather than a Glu at position 361.

4. The isolated nucleic acid of claim 3 wherein said nucleic acid is SEQ ID NO: 15 wherein base number 935 is an A rather than a G or wherein base number 1082 is a G rather than an A.

5. A nucleic acid which hybridizes specifically to the isolated nucleic acid of claim 1 or its complement under stringent hybridization conditions but will not hybridize to a nucleic acid of SEQ ID NO: 1 or SEQ ID NO: 15 under said stringent hybridization conditions.

6. The nucleic acid of claim 5 wherein said nucleic acid comprises a sequence of 8 or more consecutive bases wherein said nucleic acid comprises a base corresponding to base 941 of SEQ ID NO: 1 or its complement or base 1088 of SEQ ID NO: 1 or its complement.

7. The nucleic acid of claim 5 wherein said nucleic acid comprises a sequence of 13 or more consecutive bases wherein said nucleic acid comprises a base corresponding to base 941 of SEQ ID NO: 1 or its complement or base 1088 of SEQ ID NO: 1 or its complement.

8. A nucleic acid which hybridizes specifically to the isolated nucleic acid of claim 3 under stringent hybridization conditions but will not hybridize to a nucleic acid of SEQ ID NO: 1 or SEQ ID NO: 15 under said stringent hybridization conditions.

9. A method for diagnosing the presence or absence in a patient of a mutation which causes idiopathic dilated cardiomyopathy (IDC) wherein said method comprises hybridizing a probe of claim 5 to said patient's sample of DNA or RNA under stringent conditions which allow hybridization of said probe to nucleic acid comprising said mutation but prevent hybridization of said probe to nucleic acid of SEQ ID NO: 1 or SEQ ID NO: 15 wherein the presence of a hybridization signal indicates the presence of said mutation and wherein the absence of a hybridization signal indicates the absence of said mutation.

10. A method according to claim 9 wherein the patient's DNA or RNA has been amplified and said amplified DNA or RNA is hybridized.

11. A method according to claim 9 wherein hybridization is performed in situ.

12. A method for diagnosing in a patient the presence or absence of a mutation in cardiac actin (ACTC) which causes idiopathic dilated cardiomyopathy (IDC) wherein said method comprises: a) identifying the presence of said mutation, by single-stranded conformation polymorphism sequencing. clamped denaturing gel electrophoresis, heteroduplex analysis, chemical mismatch cleavage, allele specific oligonucleotide hybridization, restriction enzyme digestion with Southern blotting, denaturing gradient gel electrophoresis, allele specific polymerase chain reaction, amplification refractory mutation system, restriction fragment length polymorphism detection, a mutS assay, nucleic acid microchip analysis, Northern blotting, fluorescent in situ hybridization, dot blotting, or an RNAse assay and b) diagnosing said mutation in ACTC which causes IDC.

13. The method of claim 12 wherein said mutation is the presence of an A at base 941 of SEQ ID NO: 1 or a G at base 1088 of SEQ ID NO: 1.

14. The method of claim 12 wherein said means comprises using a single-stranded conformation polymorphism technique to assay for said mutation.

15. The method of claim 13 wherein said means comprises using a single-stranded conformation polymorphism technique to assay for said mutation.

16. The method of claim 12 wherein said means comprises sequencing ACTC in a sample of DNA from a patient.

17. The method of claim 13 wherein said means comprises sequencing ACTC in a sample of DNA from a patient.

18. The method of claim 16 wherein said patient's sample of DNA has been amplified or cloned.

19. The method of claim 17 wherein said patient's sample of DNA has been amplified or cloned.

20. The method of claim 12 wherein said means comprises sequencing ACTC in a sample of RNA from a patient.

21. The method of claim 13 wherein said means comprises sequencing ACTC in a sample of RNA from a patient.

22. The method of claim 12 wherein said means comprises determining the sequence of ACTC by preparing cDNA from RNA taken from said patient and sequencing said cDNA to determine the presence or absence of mutations which cause IDC.

23. The method of claim 12 wherein said means comprises performing an RNAse assay.

24. The method of claim 13 wherein said means comprises performing an RNAse assay.

25. A cell transfected with the nucleic acid of claim 1.

26. A cell transfected with the nucleic acid of claim 3.

27. A nucleic acid vector comprising a nucleic acid encoding a mutant ACTC protein wherein said mutant ACTC protein causes IDC.

28. The nucleic acid vector of claim 27 wherein said protein has a mutation selected from the group consisting of a His at amino acid residue 314 of SEQ ID NO: 2, a His at amino acid 312 of SEQ ID NO: 16, a Gly at amino acid residue 363 of SEQ ID NO: 2 and a Gly at amino acid residue 361 of SEQ ID NO: 16.

29. The vector of claim 27 wherein said vector is a replicative cloning vector.

30. The vector of claim 27 wherein said vector is an expression vector capable of directing expression of said mutant ACTC protein in host cells for said vector.

31. Host cells transformed with the vector of claim 30.

32. A pair of single-stranded oligonucleotide primers for determination of the presence of a mutation in a gene encoding ACTC wherein said mutation causes IDC wherein said primers are not complementary to wild type ACTC but are complementary to mutated ACTC encoding ACTC with HIS 312 or GLY 361.

33. The pair of primers of claim 32 wherein said pair of primers is capable of amplifying a region of nucleic acid wherein said region comprises base 941 of SEQ ID NO: 1 or base 1088 of SEQ ID NO: 1.

* * * * *

UNITED STATES PATENT AND TRADEMARK OFFICE
CERTIFICATE OF CORRECTION

PATENT NO. :  6,063,576

DATED : 16 May 2000

INVENTOR(S) : KEATING et al.

It is certified that error appears in the above-identified patent and that said Letters Patent is hereby corrected as shown below:

On the title page: Item [75]

Inventors: Mark T. Keating; [Thomas] <u>Timothy</u> M. Olson, both of Salt Lake City, Utah.

Signed and Sealed this

Third Day of April, 2001

Attest:

NICHOLAS P. GODICI

Attesting Officer    Acting Director of the United States Patent and Trademark Office